United States Patent
Kwon et al.

(10) Patent No.: US 10,456,477 B2
(45) Date of Patent: Oct. 29, 2019

(54) OLIGOLACTIC ACID CONJUGATES AND MICELLES WITH ENHANCED ANTICANCER EFFICACY

(71) Applicant: Wisconsin Alumni Research Foundation, Madison, WI (US)

(72) Inventors: Glen S. Kwon, Madison, WI (US); Yu Tong Tam, Madison, WI (US)

(73) Assignee: WISCONSIN ALUMNI RESEARCH FOUNDATION, Madison, WI (US)

( * ) Notice: Subject to any disclaimer, the term of this patent is extended or adjusted under 35 U.S.C. 154(b) by 0 days.

(21) Appl. No.: 16/084,920

(22) PCT Filed: Mar. 13, 2017

(86) PCT No.: PCT/IB2017/051455
§ 371 (c)(1),
(2) Date: Sep. 13, 2018

(87) PCT Pub. No.: WO2017/158499
PCT Pub. Date: Sep. 21, 2017

(65) Prior Publication Data
US 2019/0083633 A1    Mar. 21, 2019

Related U.S. Application Data

(60) Provisional application No. 62/307,830, filed on Mar. 14, 2016.

(51) Int. Cl.
| | |
|---|---|
| *A61K 9/00* | (2006.01) |
| *A61K 47/59* | (2017.01) |
| *A61K 47/69* | (2017.01) |
| *A61P 35/00* | (2006.01) |
| *A61K 31/337* | (2006.01) |
| *A61K 31/445* | (2006.01) |
| *A61K 31/517* | (2006.01) |
| *A61K 31/4184* | (2006.01) |

(52) U.S. Cl.
CPC .......... *A61K 47/593* (2017.08); *A61K 9/0019* (2013.01); *A61K 31/337* (2013.01); *A61K 31/4184* (2013.01); *A61K 31/445* (2013.01); *A61K 31/517* (2013.01); *A61K 47/6907* (2017.08); *A61P 35/00* (2018.01)

(58) Field of Classification Search
None
See application file for complete search history.

(56) References Cited

U.S. PATENT DOCUMENTS

| | | | |
|---|---|---|---|
| 6,395,771 B1 * | 5/2002 | Ramadoss | C07D 305/14 514/449 |
| 6,541,612 B2 * | 4/2003 | Molnar-Kimber | A61K 31/435 530/388.9 |
| 7,160,919 B2 * | 1/2007 | Holton | C07D 305/14 514/449 |
| 2011/0076308 A1 | 3/2011 | Kwon | |
| 2011/0143993 A1 | 6/2011 | Langer et al. | |

OTHER PUBLICATIONS

International Search Report re Application No. PCT/162017/051455 dated Jul. 24, 2017; 19 pages.

* cited by examiner

*Primary Examiner* — Brian J Davis
(74) *Attorney, Agent, or Firm* — Foley & Lardner LLP

(57) ABSTRACT

The present technology relates generally to oligolactic acid conjugates of paclitaxel, rapamycin, selumetinib, and other anticancer agents, micelle compositions containing such conjugates and methods of preparing and using such compositions to treat various cancers. Specifically, there are provided oligolactic acid conjugates wherein the oligolactic acid comprises 2 to 24 lactic acid subunits and is attached through an ester linkage to the oxygen of the 7-hydroxyl of the paclitaxel or paclitaxel derivative, the 40-hydroxyl of the rapamycin or rapamycin derivative, and the 2'-hydroxyl of the selumetinib or selumetinib derivative. Compositions comprising water and a micelle comprising a polylactic acid-containing polymer and the oligolactic acid conjugate may be readily prepared. Methods of inhibiting or killing cancer cells and treating paclitaxel, rapamycin, and/or selumetinib cancers are also provided.

25 Claims, 18 Drawing Sheets

OLIGOLACTIC ACID CONJUGATES AND MICELLES WITH ENHANCED ANTICANCER EFFICACY

CROSS-REFERENCE TO RELATED APPLICATIONS

This application is a U.S. national stage application under 35 U.S.C. § 371 of International Application No. PCT/IB2017/051455, filed on Mar. 13, 2017, which claims the benefit of U.S. Provisional Patent Application No. 62/307,830, filed on Mar. 14, 2016, the entire contents of each of which are incorporated herein by reference in their entireties.

GOVERNMENT RIGHTS

This invention was made with government support under AI101157 awarded by the National Institutes of Health. The government has certain rights in the invention.

FIELD

The present disclosure relates generally to oligolactic acid conjugates of taxanes such as paclitaxel and derivatives thereof, mTOR inhibitors such as rapamycin and derivatives thereof, MEK inhibitors such as selumetinib and derivatives thereof, and combinations thereof. The conjugates may be formulated in synthetic micelles to provide superior solubility, lower toxicity, and/or enhanced efficacy in the treatment of cancer compared to standard formulations of paclitaxel, rapamycin, and/or selumetinib.

BACKGROUND

Paclitaxel, rapamycin, and selumetinib are potent chemotherapeutic agents useful in the treatment of a variety of cancers and have the structures shown below.

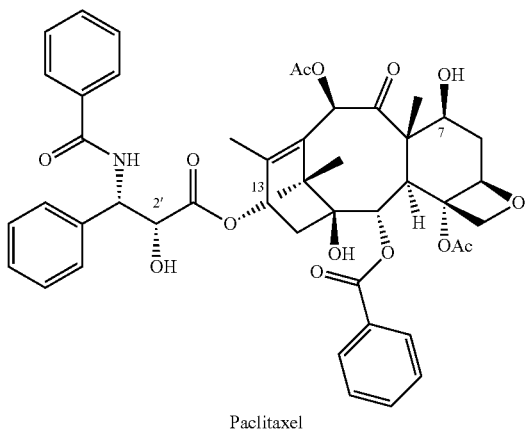

Paclitaxel

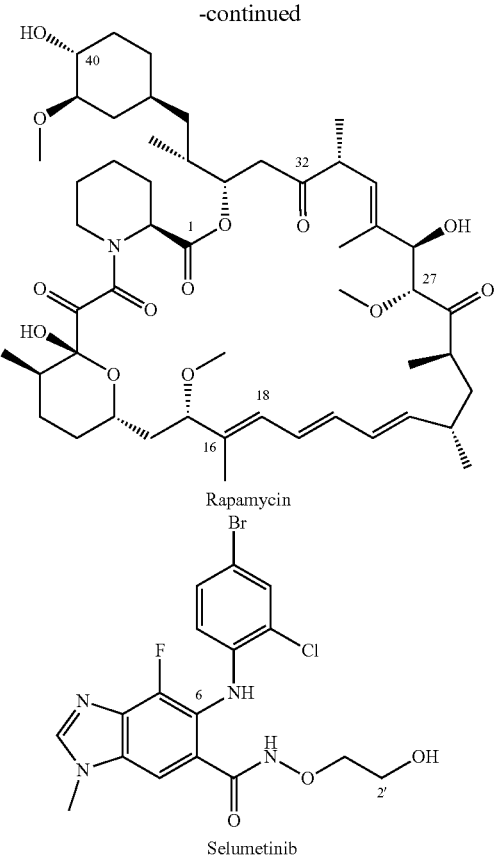

Rapamycin

Selumetinib

Due to their limited water solubility, anticancer drugs such as paclitaxel, rapamycin, and selumetinib are commonly formulated for parenteral administration with specialized vehicles that include solvents such as Cremophor® EL (CrEL), DMSO, and/or ethanol. Such non-aqueous solvents are often undesirable from a patient tolerability standpoint. CrEL for example is known to induce hypersensitivity reactions and anaphylaxis, and requires patient treatment with antihistamines and steroids before administration. Micelle compositions have been proposed as safer alternative delivery vehicles for some poorly water soluble and cytotoxic drugs. However, such compositions often suffer from low drug loading and poor stability, leading in vivo to widespread biodistribution and low tumor exposure to the drug.

SUMMARY OF THE INVENTION

The present technology provides oligolactic acid conjugates of taxanes such as paclitaxel (o(LA)$_n$-PTX) and paclitaxel derivatives (e.g., docetaxel); mTOR inhibitors such as rapamycin (o(LA)$_n$-RAP) and rapamycin derivatives (e.g., everolimus), and MEK inhibitors such as selumetinib (o(LA)$_n$-SEL) and selumetinib derivatives (e.g., binimetinib, GDC-0623, and ARRY-300). The oligolactic acid typically comprises 2 to 24 lactic acid subunits and is attached through an ester linkage to the oxygen of the 7-hydroxyl of the paclitaxel or paclitaxel derivative, the 40-hydroxyl of the rapamycin or rapamycin derivative, and the 2'-hydroxyl of the selumetinib or selumetinib derivative.

In various aspects, the present technology provides conjugates of oligolactic acid and paclitaxel or paclitaxel derivatives, rapamycin or rapamycin derivatives, and/or selumetinib or selumetinib derivatives having enhanced solubility and efficacy. The conjugates provided herein can be formulated into micelles as pharmaceutical compositions and medicaments that are useful in the treatment of cancer. Also provided is the use of the conjugates in preparing pharmaceutical formulations and medicaments.

DETAILED DESCRIPTION

The following terms are used throughout as defined below.

As used herein and in the appended claims, singular articles such as "a" and "an" and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

The present technology provides pharmaceutical compositions and medicaments comprising any of one of the embodiments of the compounds (drugs and/or drug conjugates) and micelles disclosed herein and a pharmaceutically acceptable carrier or one or more excipients. The compositions may be used in the methods and treatments described herein. The pharmaceutical composition may include an effective amount of any of one of the embodiments of the compounds of the present technology disclosed herein. In any of the above embodiments, the effective amount may be determined in relation to a subject. "Effective amount" refers to the amount of a compound, conjugate, micelle or composition required to produce a desired effect. One example of an effective amount includes amounts or dosages that yield acceptable toxicity and bioavailability levels for therapeutic (pharmaceutical) use including, but not limited to, the treatment of cancers or cardiovascular disease such as restenosis. As used herein, a "subject" or "patient" is a mammal, such as a cat, dog, rodent or primate. Typically the subject is a human, and, preferably, a human suffering from a cancer sensitive to paclitaxel, i.e. a cancer capable of treatment with an effective amount of paclitaxel. The term "subject" and "patient" can be used interchangeably.

In one aspect, the present technology provides conjugates of oligolactic acid with paclitaxel and paclitaxel derivatives.

Figure 1A:
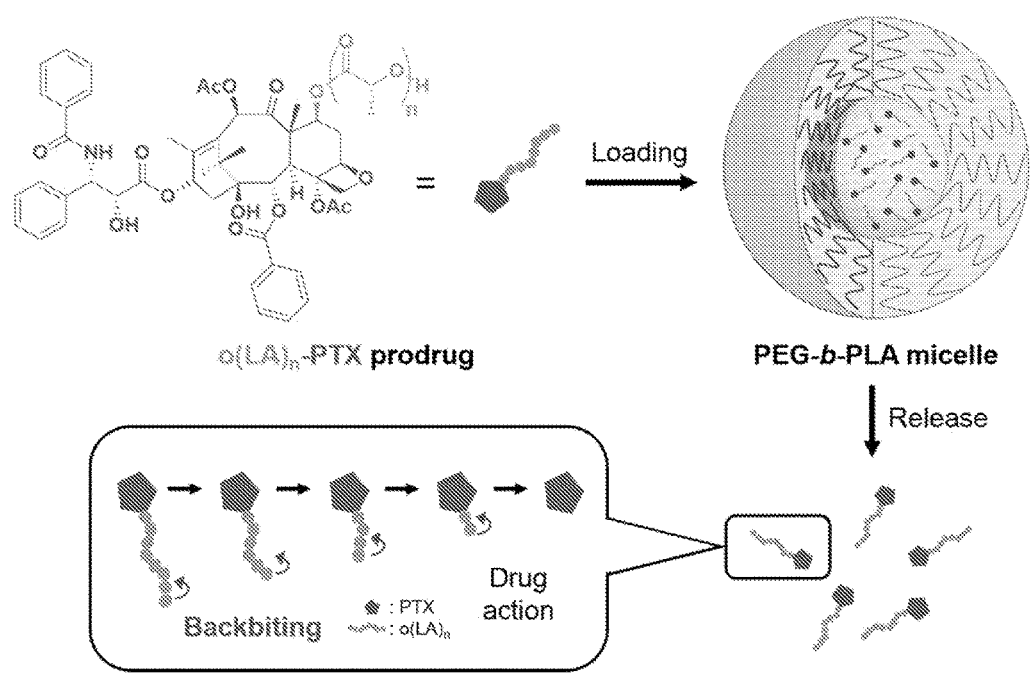
FIG. 1A shows a schematic illustrating the use of oligo (lactic acid)$_n$-paclitaxel conjugates of the present technology with poly(ethylene oxide)-block-poly(lactic acid) (PEG-b-PLA) micelles: Loading, release and backbiting conversion for anticancer activity.

As used herein, a "paclitaxel derivative" is a compound that retains the carbocyclic/oxetane skeleton of paclitaxel (i.e., the taxane skeleton) but contains at least one modified side chain other than the 7-hydroxyl. Paclitaxel derivatives of the present technology exhibit anti-cancer activity. For example, docetaxel is a paclitaxel derivative which contains a modification of the C-13 sidechain in which t-butyloxycarbonylamino replaces benzamido at the 3'-position. Other paclitaxel derivatives are known to those of skill in the art and include but are not limited to those described in Farina, V., "The chemistry and pharmacology of Taxol and its derivatives," Elsevier, New York, 1995 (incorporated herein by reference). The present conjugates and micelles exhibit enhanced solubility, stability and anti-cancer efficacy as compared with the unconjugated paclitaxel and paclitaxel derivatives. FIG. 1A illustrates schematically for one embodiment of the present technology the oligolactic acid conjugates, their loading into and release from micelles and the subsequent degradation of the conjugates to provide paclitaxel.

In one aspect, the present technology provides conjugates of oligolactic acid with rapamycin and rapamycin derivatives. As used herein, a "rapamycin derivative" or "rapalog" is a compound that retains the macrocyclic lactone ring of rapamycin, but contains at least one modified side chain while retaining a free hydroxyl group on the C-40 position or a free hydroxyl attached to a modified side chain bonded to the C-40 position (e.g., everolimus). Rapamycin derivatives of the present technology exhibit anti-cancer activity. For example, everolimus is a rapamycin derivative with the structure below. Other rapamycin derivatives are known to those of skill in the art and include but are not limited to those described in Wander, S., et al., "Next-generation mTOR inhibitors in clinical oncology: how pathway complexity informs therapeutic strategy," J. Clin. Invest., 121(4), 1231-1241 (2011) (incorporated herein by reference). The present conjugates and micelles exhibit enhanced solubility, stability and anti-cancer efficacy as compared with the unconjugated rapamycin and rapamycin derivatives. Similar to the behavior of C-7 paclitaxel conjugates of oligolactic acid, the C-40 oligolactic acid conjugates of rapamycin and its derivatives may be loaded into and released from micelles and degrade to provide rapamycin or rapamycin derivatives.

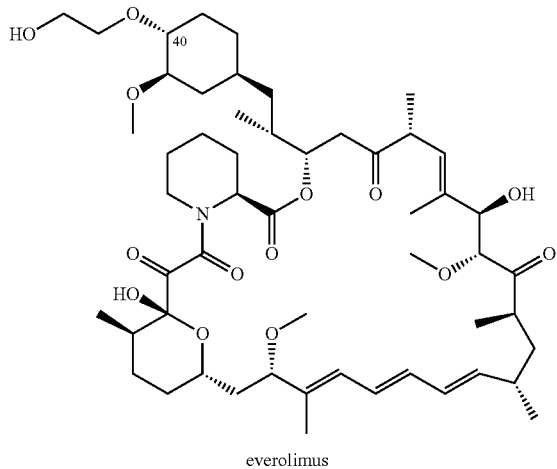 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](OCCO)[C@H](OC)C2)CC(=O)[C@H](C)/C=C(\C)[C@@H](O)[C@@H](OC)C(=O)[C@H](C)C[C@H](C)/C=C/C=C/C=C/1C]

everolimus

In one aspect, the present technology provides conjugates of oligolactic acid with selumetinib and selumetinib derivatives. As used herein, a "selumetinib derivative" is a compound that retains the 6,5-fused ring system of selumetinib, but contains at least one modified side chain while retaining a free hydroxyl group on the C-2' position (e.g., binimetinib, GDC-0623, and ARRY-300). Selumetinib derivatives of the present technology exhibit anti-cancer activity. For example, binimetinib and GDC-0623 are selumetinib derivatives with the structures below. Other selumetinib derivatives are known to those of skill in the art and include but are not limited to those described in Jokinen, E., et al., "MEK and PI3K inhibition in solid tumors: rationale and evidence to date," Ther. Adv. Med. Oncol., 7(3), 170-180 (2015) (incorporated herein by reference). The present conjugates and micelles exhibit enhanced solubility, stability and anti-cancer efficacy as compared with the unconjugated selumetinib and selumetinib derivatives. Similar to the behavior of C-7 paclitaxel conjugates of oligolactic acid, the C-2' oligolactic acid conjugates of selumetinib and its derivatives may be loaded into and released from micelles and degrade to provide selumetinib or selumetinib derivatives.

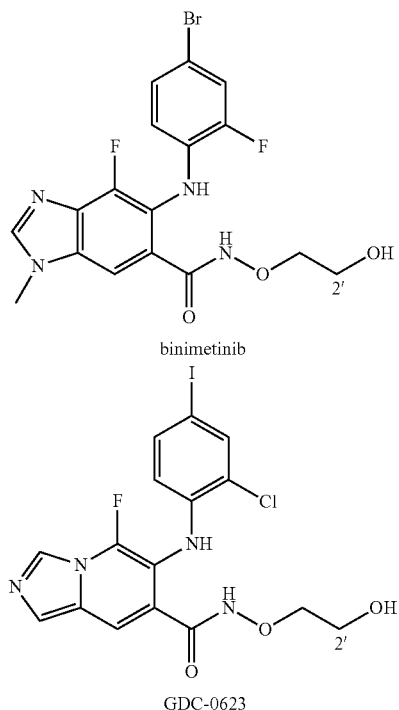

In the present conjugates, oligolactic acid is a linear polyester of lactic acid and is attached through an ester linkage to the oxygen of the 7-hydroxyl of the paclitaxel or paclitaxel derivative (herein the "7-oligolactic acid conjugate"), the oxygen of the 40-hydroxyl of the rapamycin or rapamycin derivative (herein the "40-oligolactic acid conjugate"), and/or the oxygen of the 2'-hydroxyl of the selumetinib or selumetinib derivative (herein the "2'-oligolactic acid conjugate"). In such oligolactic acid conjugates, the oligolactic acid typically includes 2 to 24 lactic acid subunits. It will be understood by those skilled in the art that the present conjugates may have 2, 3, 4, 5, 6, 7, 8, 9, 10, 11, 12, 13, 14, 15, 16, 17, 18, 19, 20, 21, 22, 23, or 24 lactic acid subunits or a range of subunits between any two of the foregoing values. For example, the oligolactic acid may include 4 to 20, 6 to 18, or 2 to 10 lactic acid subunits. In some embodiments, the conjugates have the structures shown in formulas I, II, and/or III:

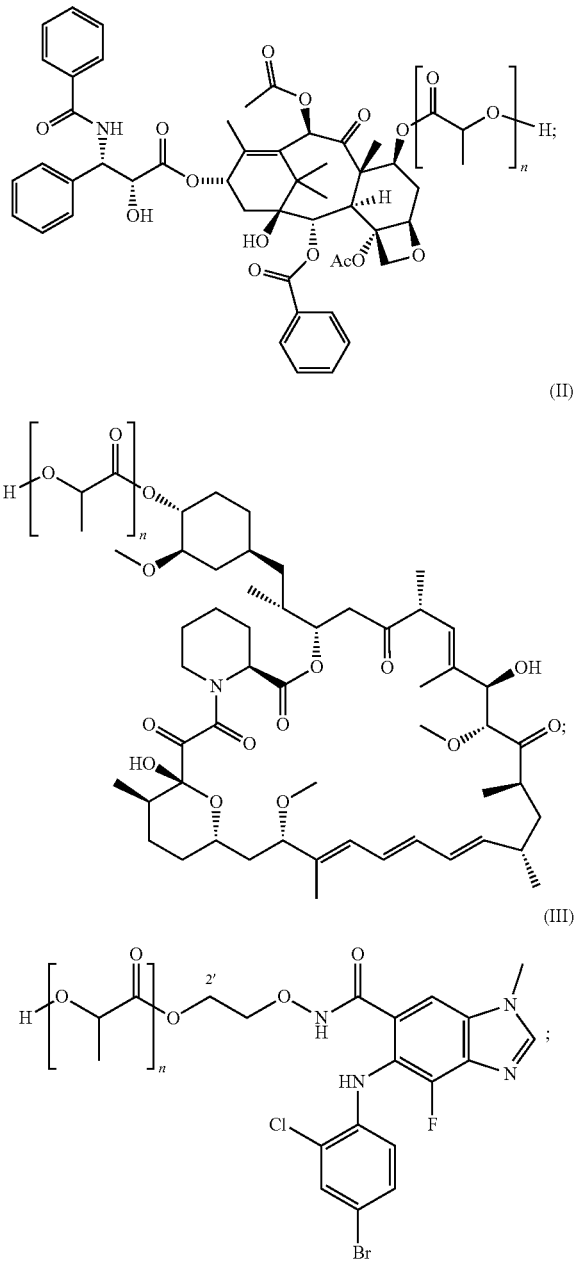

wherein n at each occurrence is individually an integer from 2 to 24 or a range between and including any two values selected from 2, 3, 4, 5, 6, 7, 8, 9, 10, 11, 12, 13, 14, 15, 16, 17, 18, 19, 20, 21, 22, 23, and 24. In some embodiments, n at each occurrence is individually an integer from 4 to 20. In some embodiments, n at each occurrence is individually an integer from 6 to 18. In some embodiments the oligolactic acid is D,L-oligolactic acid. In others it is L-oligolactic acid, and in still others, it is D-oligolactic acid.

Figure 1B:
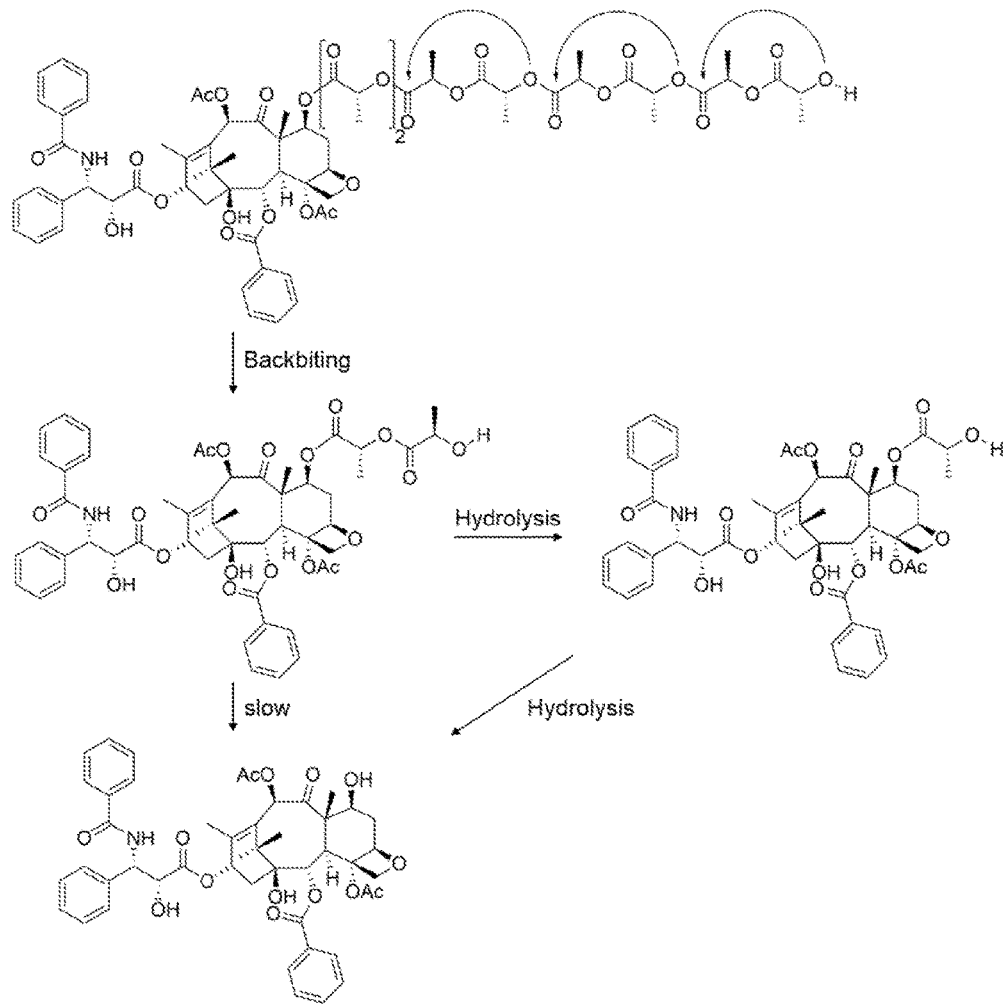
FIG. 1B shows a chemical scheme illustrating a likely backbiting degradation mechanism for an illustrative embodiment of the present conjugates.

Conjugates of the present technology advantageously serve as prodrugs for paclitaxel, rapamycin, and selumetinib in vivo. Under conditions mimicking those in vivo, i.e., a pH near neutral, the oligolactic acid sidechain self-degrades predominantly in a controlled stepwise fashion rather than by random hydrolysis and is independent of, e.g., esterases. While not wishing to be limited by theory, as shown in FIG. 1B, the degradation of the conjugates is believed to occur by a "backbiting" mechanism in which the free hydroxyl group at the terminus of the oligolactic acid attacks the ester linkage formed by the carbonyl of the adjacent lactic acid subunit. In this way lactoyllactate dimers are released until only one or two subunits of lactic acid remain attached to the drug/drug derivative; the last two subunits are subject to slow backbiting and only slowly hydrolyze over time. This stepwise mechanism is consistent with the HPLC profiles observed for the in vitro degradation over time of o(LA)$_8$-PTX and o(LA)$_{16}$-PTX (see FIGS. 2A and 2B), o(LA)$_8$-RAP (see FIG. 10A), and o(LA)$_8$-SEL (see FIG. 10B).

Figure 3:
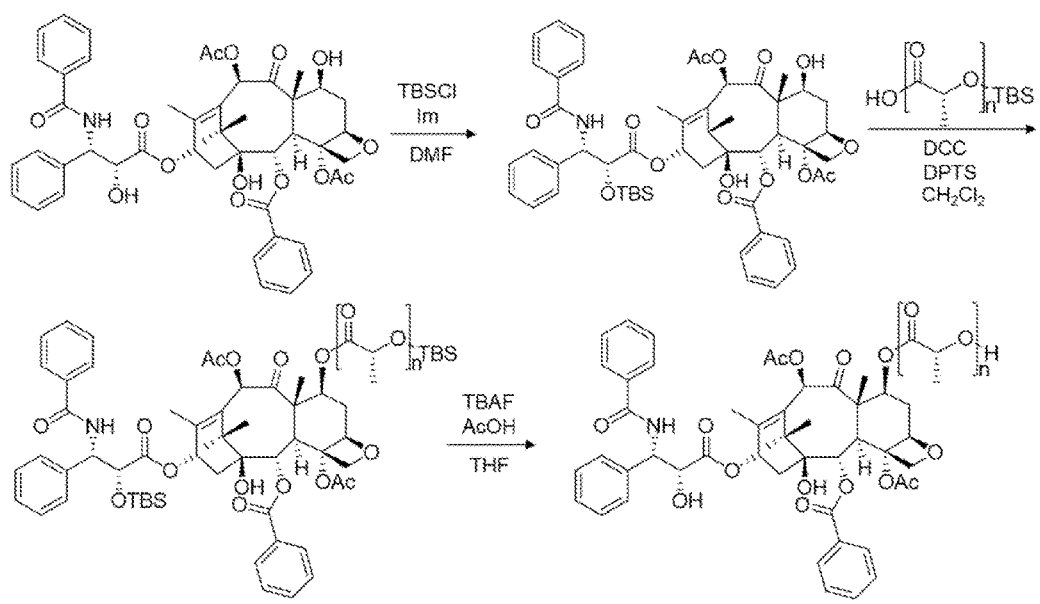
FIG. 3 provides an illustrative synthetic scheme for producing o(LA)$_n$-PTX conjugates.
Figure 9A:
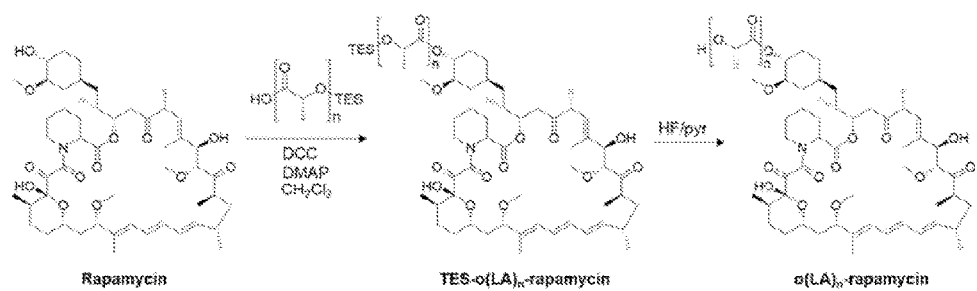
FIG. 9A provides an illustrative synthetic scheme for producing o(LA)$_n$-RAP conjugates.
Figure 9B:
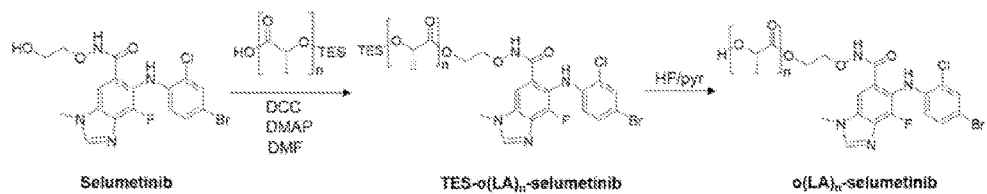
FIG. 9B provides an illustrative synthetic scheme for producing o(LA)$_n$-SEL conjugates.

The 7-oligolactic acid conjugate disclosed herein may be prepared by contacting paclitaxel or a paclitaxel derivative having a free 7-hydroxyl group with a coupling agent and a mono-O-silylated oligolactic acid having 2 to 24 lactic acid subunits. Similarly, the 40-oligolactic acid and 2'-oligolactic acid may be prepared by contacting rapamycin or a rapamycin derivative having a free 40-hydroxyl group or selumetinib or a selumetinib derivative having a free 2'-hydroxyl group, respectively, with a coupling agent and a mono-O-silylated oligolactic acid having 2 to 24 lactic acid subunits. By way of example only, FIGS. 3, 9A, and 9B show illustrative embodiments of methods of making the present conjugates. In FIG. 3, the 2'-hydroxyl of paclitaxel is protected by reacting paclitaxel with a silylation agent such as t-butyldimethyl silyl chloride, optionally in the presence of a catalyst such as imidazole in a polar aprotic solvent such as DMF. The protected paclitaxel is coupled to a hydroxyl-protected oligolactic acid intermediate using a coupling reagent in a suitable organic solvent. Similarly, in FIGS. 9A and 9B, rapamycin and selumetinib are coupled to a hydroxyl-protected oligolactic acid intermediate using a coupling reagent in a suitable organic solvent. Suitable coupling agents include carbodiimides such as DCC and EDCI. Suitable organic solvents include halogenated solvents (e.g., dichloromethane, chloroform), alkyl acetate (e.g., ethyl acetate), or other polar aprotic solvent (e.g., DMF). The coupling reaction will typically also include a catalyst such as 4-(dimethylamino)-pyridinium p-toluenesulfonate (DPTS) or 4-(dimethyl-amino)pyridine (DMAP). In some embodiments, the hydroxyl-protected oligolactic acid is O-silylated oligolactic acid, e.g., O-t-butyldimethylsilyl (OTBS) oligolactic acid or O-triethylsilyl (OTES) oligolactic acid. While other known hydroxyl protecting groups may be used, the silyl groups on the paclitaxel 2' hydroxyl and on the oligolactide hydroxyl are conveniently removed with fluoride. For example, FIG. 3 shows that deprotection of the TBS groups with tetrabutylammonium fluoride in acetic acid and THF provides the desired conjugate and FIGS. 9A and 9B show deprotection of the TES group with hydrofluoric acid and pyridine provide the desired conjugates.

Monodisperse mono-O-silylated oligolactic acid may be prepared using known methods such as ring opening of cyclic lactide (including cyclic L-lactide) followed by protection-coupling-deprotection sequences to afford monofunctional oligomers, e.g., using TBS ether or TES ether and benzyl ester as protective groups for hydroxyl and carboxylic acid groups, respectively. Other suitable triorganosilyl chloride agents may be used in place of t-butyldimethylsilyl chloride and triethylchlorosilane, such as, but not limited to, trimethylsilyl chloride, i-propyl-dimethylchlorosilane, chlorotribenzylsilane, chlorotributylsilane, chlorotriisopropylsilane, chlorotrihexylsilane, chlorotriisobutylsilane and chlorotriphenylsilane. In addition to benzyl ester, or any esters orthogonal to the silyl groups may also be used. Alternatively, mono-disperse oligolactic acids may be prepared by traditional polymerization techniques followed by separation by reverse phase column chromatography or gel filtration.

In another aspect, the present technology provides aqueous compositions of micelles formed from water; polylactic acid-containing polymers; and the 3-drug combination of a free paclitaxel/paclitaxel derivative, a free rapamycin/rapamycin derivative, and a free selumetinib/selumetinib derivative. As used herein, the term "free" refers to the unconjugated drug/drug derivatives. Such micelles are typically more stable than the corresponding micelles individually loaded with free paclitaxel/paclitaxel derivatives, free rapamycin/rapamycin derivatives, or free selumetinib/selumetinib derivatives (see Table 2).

Micelles which include the 3-drug combination of free paclitaxel/paclitaxel derivative, free rapamycin/rapamycin derivative, and free selumetinib/selumetinib derivative are capable of higher drug loading than when the free drugs/drug derivatives are loaded alone (see Tables 1-2). For example, free selumetinib loads alone in micelles at only about 1 wt % and precipitates after a short period of time (about 5 minutes). In contrast, free selumetinib loaded in micelles with free paclitaxel and free rapamycin have a drug loading of greater than 6 wt % with increased micelle stability (see Tables 1 and 2). In some embodiments, the loading of free paclitaxel/paclitaxel derivatives may be from about 1 wt % to about 10 wt % including about 2 wt % to about 6 wt % with respect to the mass of the micelles. In some embodiments, the loading of free rapamycin/rapamycin derivatives may be from about 1 wt % to about 10 wt % including about 1 wt % to about 4 wt % with respect to the mass of the micelles. In some embodiments, the loading of free selumetinib/selumetinib derivatives may be from about 1 wt % to about 10 wt % including about 4 wt % to about 8 wt % with respect to the mass of the micelles. Examples of total free drug loading in the micelles may be about 5 wt % to about 20 wt % including about 7 wt %, about 10 wt %, about 13 wt %, about 15 wt %, about 18 wt %, with respect to the mass of the micelles, or a range between and including any two of the foregoing values.

Figure 4:
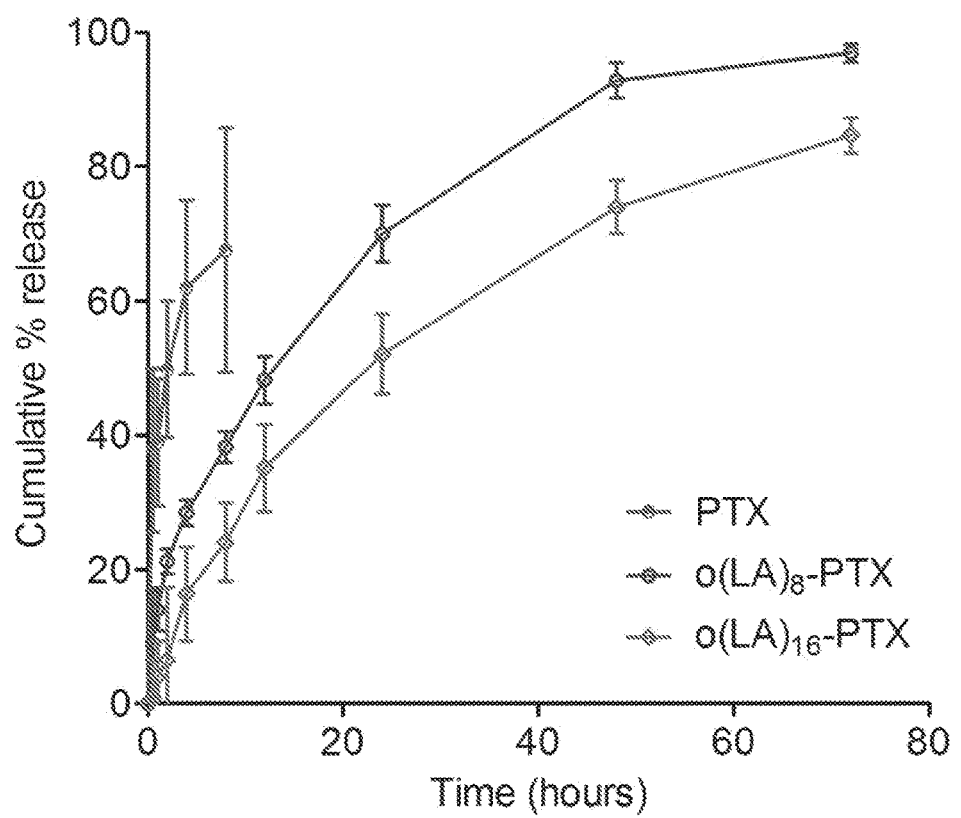
FIG. 4 shows the time course for in vitro release of PTX, o(LA)$_8$-PTX or o(LA)$_{16}$-PTX from PEG-b-PLA micelles (mean±SD, n=3).

In another aspect, the present technology provides aqueous compositions of micelles formed from water, polylactic acid-containing polymers and any of the present oligolactic acid-drug/drug derivative conjugates (i.e., paclitaxel/paclitaxel derivative conjugates, rapamycin/rapamycin derivative conjugates, and/or selumetinib/selumetinib derivative conjugates). Such micelles are generally more stable than the corresponding micelles with the free drug/drug derivatives. For example, as shown in FIG. 4, micelles formed from poly(ethylene glycol)-block-polylactic acid and one of o(LA)$_8$-PTX or o(LA)$_{16}$-PTX, release the conjugates much more slowly than they release free paclitaxel. In some embodiments, the present technology provides aqueous compositions of micelles formed from water, polylactic acid-containing polymers and the 3-drug combination of a paclitaxel/paclitaxel derivative conjugate, a rapamycin/rapamycin derivative conjugate, and a selumetinib/selumetinib derivative conjugate.

In some embodiments of the present technology, the micelles include the block copolymer, PEG-b-PLA (also known as PEG-PLA). The poly(lactic acid) block can include (D-lactic acid), (L-lactic acid), (D,L-lactic acid), or combinations thereof. Various forms of PEG-b-PLA are available commercially, such as from Polymer Source, Inc., Montreal, Quebec, or they can be prepared according to methods well known to those of skill in the art. The molecular weight of the poly(ethylene glycol) block can be about 1,000 to about 35,000 g/mol, or any increment of about 500 g/mol within said range. (All polymer molecular weights referred to herein will be understood to be weight average molecular weights.) For example, the molecular weight of the PEG block may be 1,000, 1,500, 2,000, 2,500, 3,000, 3,500, 4,000, 4,500, 5,000, 6,000, 7,000, 8,000, 9,000, 10,000, 11,000, 12,000, 13,000, 14,000, 15,000, 16,000, 17,000, 18,000, 19,000, 20,000, 21,000, 22,000, 23,000, 24,000, 25,000, 26,000, 27,000, 28,000, 29,000, 30,000, 31,000, 32,000, 33,000, 34,000, 35,000 or a range between and including any two of the foregoing values. Suitable blocks of the poly(lactic acid) can have molecular weights of about 1,000 to about 15,000 g/mol, or any increment of about 500 g/mol within said range. For example, the molecular weight of the PEG block may be 1,000, 1,500, 2,000, 2,500, 3,000, 3,500, 4,000, 4,500, 5,000, 6,000, 6,500, 7,000, 7,5000, 8,000, 8,500, 9,000, 9,500, 10,000, 10,500, 11,000, 11,500, 12,000, 12,500, 13,000, 13,500, 14,000, 14,500, 15,000, or a range between and including any two of the foregoing values. The PEG block can terminate in an alkyl group, such as a methyl group (e.g., a methoxy ether) or any suitable protecting, capping, or blocking group. In some embodiments, the molecular weight of the poly(ethylene glycol) block of PEG-b-PLA is about 1,000 to about 35,000 g/mol and the molecular weight of the poly(lactic acid) block of PEG-b-PLA is about 1,000 to about 15,000 g/mol. In some embodiments, the molecular weight of the poly(ethylene glycol) block is about 1,500 to about 14,000 g/mol, and the molecular weight of the poly(lactic acid) block is about 1,500 to about 7,000 g/mol.

The micelles of this disclosure can be prepared using PEG-b-PLA polymers of a variety of block sizes (e.g., a block size within a range described above) and in a variety of ratios. For example, the PEG:PLA ratio may be about 1:10 to about 10:1, or any integer ratio within said range, including without limitation 1:5, 1:3, 1:2, 1:1, 2:1, 3:1, and 5:1. For example, weight average molecular weights ($M_a$) of the PEG-PLA polymers can include, but are not limited to, 2K-2K, 3K-5K, 5K-3K, 5K-6K, 6K-5K, 6K-6K, 8K-4K, 4K-8K, 12K-3K, 3K-12K, 12K-6K, 6K-12K (PEG-PLA, respectively) or a range between and including any two of the foregoing values.

One suitable PLA-containing polymer is a PEG-PLA that includes blocks of about 1-3 kDa (e.g., about 2K Daltons) at an approximate 50:50 ratio. Use of this procedure resulted in high levels of drug-conjugate loading in the micelles. Further specific examples of PEG-PLA molecular weights include 4.2K-b-1.9K; 5K-b-10K; 12K-b-6K; 2K-b-1.8K, and those described in the Examples below. Other suitable amphiphilic block copolymers that may be used are described in U.S. Pat. No. 4,745,160 (Churchill et al.) and U.S. Pat. No. 6,322,805 (Kim et al.). The drug-to-polymer ratio may be about 1:20 to about 2:1, or any integer ratio within said range. Specific examples of suitable drug-polymer ratios include, but are not limited to, about 2:1, about 3:2, about 1.2:1, about 1:1, about 3:5, about 2:5, about 1:2, about 1:5; about 1:7.5; about 1:10, about 1:20 or a range between and including any of the foregoing values.

Micelles of the present technology may be loaded with a wide range of amounts, including high amounts, of the conjugates described herein, especially in comparison to the same micelles with free drug/drug conjugates alone. For example, the loading of the conjugates may be from about 2 wt % to about 60 wt % with respect to the mass of the micelles. Examples of conjugate loading in the micelles include about 3 wt %, about 4 wt %, about 5 wt %, about 10 wt %, about 15 wt %, about 20 wt %, about 25 wt %, about 30 wt %, about 35 wt %, about 40 wt %, about 45 wt %, about 50 wt %, about 55 wt %, or about 60 wt % with respect to the mass of the micelles, or a range between and including any two of the foregoing values. In some embodiments, the loading of the 7-oligolactic acid conjugate (of paclitaxel/paclitaxel derivative) may be from about 5 wt % to about 60 wt % including about 8 wt % to about 55 wt %, the loading of the 40-oligolactic acid conjugate (of rapamycin/rapamycin derivative) may be from about 5 wt % to about 50 wt % including about 7 wt % to about 45 wt %, and/or the loading of the 2'-oligolactic acid conjugate (of selumetinib/selumetinib derivative) may be from about 2 wt % to about 30 wt % including about 4 wt % to about 25 wt %.

Loading of each conjugate in the micelles may also be expressed in terms of concentration. For example, the concentration of each conjugate may be from about 0.5 mg/mL to about 40 mg/mL with respect to the volume of the water in the composition. Examples of each conjugate concentration that may be obtained with the present technology include about 0.6, about 1 mg/mL, about 2 mg/mL, about 3 mg/mL, about 4 mg/mL, about 5 mg/mL, about 6 mg/mL, about 8 mg/mL, about 10 mg/mL, about 12 mg/mL, about 15 mg/mL, about 20 mg/mL, about 25 mg/mL, about 30 mg/mL, about 35 mg/mL, or about 40 mg/mL with respect to the volume of the water in the composition, or a range between and including any two of the foregoing values. In some embodiments, the concentration of the 7-oligolactic acid conjugate may be about 1 to about 15 mg/mL or even about 2 to about 12 mg/mL, the concentration of the 40-oligolactic acid conjugate may be about 1 to about 20 mg/mL or even about 1.5 to about 10 mg/mL, and/or the concentration of the 2'-oligolactic acid conjugate may be about 0.5 to about 15 mg/mL or even about 1 to about 10 mg/mL.

The loading of each conjugate in the micelles may also be expressed in terms of loading efficiency. For example, the loading efficiency of each conjugate may be from about 25 wt % to about 100 wt % with respect to the mass of the micelles. Examples of conjugate loading efficiency in the micelles include about 30 wt %, about 35 wt %, about 40 wt %, about 45 wt %, about 50 wt %, about 55 wt %, about 60 wt %, about 65 wt %, about 70 wt %, about 75 wt %, about 80 wt %, about 85 wt %, about 90 wt %, about 95 wt %, about 99 wt %, or about 100 wt % with respect to the mass of the micelles, or a range between and including any two of the foregoing values. In some embodiments, the loading efficiency of the 7-oligolactic acid conjugate may be at least about 85 wt % including about 90 wt % to about 100 wt %, the loading efficiency of the 40-oligolactic acid conjugate may be at least about 75 wt % including from about 80 wt % to about 90 wt %, and/or the loading efficiency of the 2'-oligolactic acid conjugate may be at least about 25 wt % including from about 30 wt % to about 55 wt %.

In some embodiments, the present technology provides compositions comprising water and a micelle including PEG-b-PLA and at least one of the 7-oligolactic acid conjugates, the 40-oligolactic acid conjugates, and the 2'-oligolactic acid conjugates described herein, wherein the loading of the 7-oligolactic acid conjugate in the micelle is from about 1 wt % to about 60 wt %, the loading of the 40-oligolactic acid conjugate is from about 1 wt % to about 50 wt %; and/or the loading of the 2'-oligolactic acid conjugate is from about 1 wt % to about 30 wt % with respect to the mass of the micelles; the molecular weight of the poly(ethylene glycol) block of the PEG-b-PLA is about 1,500 to about 14,000 g/mol; and the molecular weight of the poly(lactic acid) block of the PEG-b-PLA is about 1,500 to about 7,000 g/mol. Such compositions may include any of the drug loadings described herein, including e.g., about 5 wt % to about 60 wt %, or about 1 to about 15 mg/mL or even about 2 to about 12 mg/mL of any of the 7-oligolactic acid conjugates; about 5 wt % to about 50 wt %, or about 1 to about 20 mg/mL or even about 2 to about 10 mg/mL of any of the 40-oligolactic acid conjugates; and about 2 wt % to about 30 wt %, or about 1 to about 15 mg/mL or even about 2 to about 15 mg/mL of any of the 2'-oligolactic acid conjugates. In some embodiments, the composition may include any of the 7-oligolactic acid conjugates, the 40-oligolactic acid conjugates, and the 2'-oligolactic acid conjugates as described herein.

Amphiphilic single chains of amphiphilic polymers present in a solvent in an amount above the critical micelle concentration (CMC) aggregate into a micelle, a core-coronal structure with a hydrophobic interior, and hydrophilic exterior or shell. Proton NMR spectroscopic studies of drug or conjugate loaded PEG-b-PLA micelles indicate that while the micelles readily form in aqueous environments, they decompose in organic solvents such as DMSO. The present micelle compositions typically are substantially free of organic solvents, e.g., less than about 2 wt % of ethanol, dimethyl sulfoxide, castor oil, and castor oil derivatives (i.e., polyethoxylated camphor compounds such as Cremophor EL) based on the weight of the composition. In some embodiments the amount of organic solvent is less than about 1 wt %, less than about 0.5 wt %, less than about 0.1 wt % or essentially free of detectable amounts of organic solvents.

PEG-b-PLA micelles can be prepared as described below in this section, as well as below in the Examples. The composition of micelles described herein may be prepared by combining water with a mixture of a polylactic acid-containing polymer and the 3-drug/drug derivative combination of paclitaxel, rapamycin, and selumetinib. In another embodiment, the composition of micelles described herein may be prepared by combining water with a mixture of a polylactic acid-containing polymer and at least one of the drug/drug derivative conjugates described herein. In some embodiments, the polylactic acid-containing polymer is PEG-b-PLA.

The procedures given below are merely illustrative. Each can be varied according to the desired scale of preparation, as would be readily recognized by one skilled in the art. One advantage of Preparatory Procedures A, B and D is that they do not require dialysis of a micelle solution, as in Procedure C. Other procedures that can be used include oil in water emulsions and those described by Gaucher et al., *J. Controlled Release*, 109 (2005) 169-188.

Preparatory Procedure A: Simple Equilibrium. In one embodiment, micelle preparation can be carried out as follows. PEG-b-PLA and at least one oligolactic acid conjugate as described herein is dissolved in a suitable water miscible solvent, such as acetonitrile or dimethylacetamide, with optional mixing and/or sonication. The conjugate(s) may be mono-disperse with respect to the oligolactic acid or may have a range of oligolactic acids of different lengths. The solvent is then removed, for example under reduced pressure to provide a polymer-drug thin film. Warm sterile water (approximately 50° C. to about 70° C.) is added to the polymer-drug conjugate film and the mixture is allowed to cool. The conjugate(s) encapsulating polymeric micelles form upon addition of warm water and then can be isolated, for example, by filtration.

Preparatory Procedure B: Simple Equilibrium. At least one drug conjugate as described herein and PEG-b-PLA (at a ratio of, e.g. 1:7 to 1:10) are dissolved in 2.5-5 mL of acetonitrile. The mixture is mixed and sonicated for five minutes. The solvent is then removed by rotoevaporation at approximately 60° C. to provide a film. Hot (~60° C.) deionized water is added to the oil and the solution is allowed to cool to ~23° C. The solution is then centrifuged to remove the sediment in a 1.5 mL microtube, at ~15,000 rpm for ~5 minutes. The supernatant is collected and filtered through a 0.2 µm PTFE filter. The isolated micelles can then be stored for extended periods of time at 4° C.

Preparatory Procedure C: Dialysis. In another embodiment, the micelles can be loaded and formed by the following dialysis procedure. PEG-b-PLA and at least one drug conjugate as described herein of the desired ratio (e.g., varying from 1:20 to 20:1) are dissolved in a water miscible solvent, such as dimethylacetamide. The mixture is then added to an aqueous solution, such as a 0.9% saline, in a 3500 MWCO tubing (Spectra/Por®) dialysis bag, whereupon the micelles form, incorporating the drug conjugate(s). The micelle mixture can then be centrifuged (e.g., at ~16,000 rpm for 5 minutes) to precipitate any unincorporated drug conjugate(s). The supernatant can then nanofiltered, and analysis can be carried out using HPLC, such as with UV and RI detection modes (see the techniques described by Yasugi et al., *J. Control. Release*, 1999, 62, 99-100).

Preparatory Procedure D: Freeze-drying. At least one drug conjugate as described herein loaded in a PEG-b-PLA micelle can be prepared by freeze-drying from a tert-butanol-water mixture. For example, 2-20 mg of PEG4000-b-PLA2200 (Advanced Polymer Materials Inc., Montreal, Canada) and 1.0 mg of a conjugate(s) as described herein can be dissolved in 1.0 mL of tert-butanol at 60° C., followed by addition of 1.0 mL of pre-warmed double-distilled water at 60° C. with vigorous mixing. The mixture is allowed to freeze in dry ice/ethanol cooling bath at −70° C. Lyophilization may then be performed on a shelf freeze-dryer at −20° C. shelf inlet temperature for 72 h at 100 µBar throughout the experiment. The lyophilized cake may then rehydrated with 1.0 mL of 0.9% saline solution at 60° C., centrifuged, filtered through 0.22 µm regenerated cellulose filter, and analyzed by HPLC.

Similarly, the PEG-b-PLA micelles loaded with free drugs can be prepared as described in any of Preparatory Procedures A-D, as well as below in the Examples by substituting the conjugate(s) with the 3-free drug combination of paclitaxel/paclitaxel derivative, rapamycin/rapamycin derivative, and selumetinib/selumetinib derivative.

Once prepared, the micelle-conjugate or micelle-drug compositions can be stored for extended periods of time under refrigeration, preferably at a temperature below about 5° C. Temperatures between about −20° C. and about 4° C. have been found to be suitable conditions for storage of most micelle-conjugate and micelle-drug compositions. For example, aqueous solutions of the present conjugate-loaded micelles may be stored at about 4° C. Freeze-dried micelle compositions as described herein can be stored at −20° C. for prolonged periods and then rehydrated. Use of brown glass vials or other opaque containers to protect the micelle compositions from light can further extend effective lifetimes of the compositions.

In another aspect, the present technology provides methods of inhibiting or killing cancer cells sensitive to paclitaxel or a paclitaxel derivative, rapamycin or a rapamycin derivative, and/or selumetinib or a selumetinib derivative comprising contacting the cells with an effective inhibitory or lethal amount of any of the compositions described herein. In some such methods, the contacting is performed in vitro or in vivo. There are also provided methods of treatment including administering to a mammal suffering from a cancer sensitive to paclitaxel or a paclitaxel derivative, rapamycin or a rapamycin derivative, and/or selumetinib or a selumetinib derivative, an effective amount of any of the micelle compositions described herein. Examples of paclitaxel-sensitive, rapamycin-sensitive, and selumetinib-sensitive cancers include brain tumors, breast cancer, colon cancer, head and neck cancer, lung cancer, lymphoma, melanoma, neuroblastoma, ovarian cancer, pancreatic cancer, prostate cancer, angiosarcoma, and leukemia. In some embodiments, the cancer is breast cancer or lung cancer. In some embodiments, the effective amounts of two or three drug/drug derivative or drug/drug derivative conjugate as disclosed herein are synergistic, e.g., they have a more than additive effect or produce effects that cannot produced by a drug or drug conjugate alone.

In any of the embodiments of the present technology described herein, the pharmaceutical composition may be packaged in unit dosage form. The unit dosage form is effective in treating a cancer or restenosis. Generally, a unit dosage including a composition of the present technology will vary depending on patient considerations. Such considerations include, for example, age, protocol, condition, sex, extent of disease, contraindications, concomitant therapies and the like. An exemplary unit dosage based on these considerations can also be adjusted or modified by a physician skilled in the art. For example, a unit dosage for a patient comprising a compound of the present technology can vary from $1\times10^{-4}$ g/kg to 1 g/kg, preferably, $1\times10^{-3}$ g/kg to 1.0 g/kg. Dosage of a compound of the present technology can also vary from 0.01 mg/kg to 100 mg/kg or, preferably, from 0.1 mg/kg to 10 mg/kg.

Micelle compositions containing conjugates of paclitaxel or paclitaxel derivatives, rapamycin or rapamycin derivative, and/or selumetinib or selumetinib derivative may be prepared as described herein and used to treat cancers and cardiovascular diseases. The conjugates and compositions described herein may be used to prepare formulations and medicaments that treat restenosis or a cancer, such as leukemia, angiosarcoma, breast cancer, colorectal cancer, prostate cancer, lung cancer, brain cancer (such as gliomas), adenocarcinomas, or hepatomas. Such compositions can be in the form of, for example, granules, powders, tablets, capsules, syrup, suppositories, injections, emulsions, elixirs, suspensions or solutions. The instant compositions can be formulated for various routes of administration, for example, by parenteral, rectal, nasal, vaginal administration, or via implanted matrix or reservoir, or for restenosis, by drug-coated stent or balloon-based delivery. Parenteral or systemic administration includes, but is not limited to, subcutaneous, intravenous, intraperitoneal, and intramuscular, injections. The following dosage forms are given by way of example and should not be construed as limiting the instant present technology.

Injectable dosage forms generally include solutions or aqueous suspensions or oil in water suspensions which may be prepared using a suitable dispersant or wetting agent and a suspending agent. Injectable forms may be in solution phase or in the form of a suspension, which is prepared with a solvent or diluent. Acceptable solvents or vehicles include sterilized water, Ringer's solution, or an isotonic aqueous saline solution.

For injection, the pharmaceutical formulation and/or medicament may be a film or powder suitable for reconstitution with an appropriate solution as described above. Examples of these include, but are not limited to, freeze dried, rotary dried or spray dried powders, amorphous powders, granules, precipitates, or particulates. For injection, the formulations may optionally contain stabilizers, pH modifiers, surfactants, bioavailability modifiers and combinations of these. In some embodiments, the injectable formulations include an isotonicity agent (e.g., NaC 1 and/or dextrose), buffer (e.g., phosphate) and/or a preservative.

Besides those representative dosage forms described above, pharmaceutically acceptable excipients and carriers are generally known to those skilled in the art and are thus included in the instant present technology. Such excipients and carriers are described, for example, in "Remingtons Pharmaceutical Sciences" Mack Pub. Co., New Jersey (1991), which is incorporated herein by reference.

The formulations of the present technology may be designed to be short-acting, fast-releasing, long-acting, and sustained-releasing as described below. Thus, the pharmaceutical formulations may also be formulated for controlled release or for slow release.

Specific dosages may be adjusted depending on conditions of disease, the age, body weight, general health conditions, sex, and diet of the subject, dose intervals, administration routes, excretion rate, and combinations of free drugs/conjugates. Any of the above dosage forms containing effective amounts are well within the bounds of routine experimentation and therefore, well within the scope of the instant present technology. By way of example only, such dosages may be used to administer effective amounts of the free drugs/conjugates to the patient and may include about 10 mg/m$^2$, about 20 mg/m$^2$, about 30 mg/m$^2$, about 40 mg/m$^2$, about 50 mg/m$^2$, about 75 mg/m$^2$, about 100 mg/m$^2$, about 125 mg/m$^2$, about 150 mg/m$^2$, about 200 mg/m$^2$, about 250 mg/m$^2$, about 300 mg/m$^2$, or a range between and including any two of the forgoing values. Such amounts may be administered parenterally as described herein and may take place over a period of time including but not limited to 5 minutes, 10 minutes, 20 minutes, 30 minutes, 45 minutes, 1 hour, 2 hours, 3 hours, 5 hours, 10 hours, 12, hours, 15 hours, 20 hours, 24 hours or a range between and including any of the foregoing values. The frequency of administration may vary, for example, once per day, per 2 days, per 3 days, per week, per 10 days, per 2 weeks, or a range between and including any of the foregoing frequencies.

For each of the indicated conditions described herein, test subjects will exhibit a 10%, 20%, 30%, 50% or greater reduction, up to a 75-90%, or 95% or greater, reduction, in one or more symptom(s) caused by, or associated with, the disorder in the subject, compared to placebo-treated or other suitable control subjects.

In a related aspect, method for treating a subject is provided, where the method involves administration of any one of the embodiments of the compositions of the present technology to a subject suffering from a cancer or a cardiovascular disease. In the method, it may be that the cancer is leukemia, angiosarcoma, breast cancer, colorectal cancer, prostate cancer, lung cancer, brain cancer (such as gliomas), adenocarcinomas, or hepatomas.

In any of the embodiments of the method, the method may involve administration of a pharmaceutical composition, where the pharmaceutical composition includes any one of the embodiments of the conjugates or micelles containing the free drugs or conjugates of the present technology as well as a pharmaceutically acceptable carrier.

The examples herein are provided to illustrate advantages of the present technology and to further assist a person of ordinary skill in the art with preparing or using the conjugates and micelle compositions of the present technology, pharmaceutical compositions, derivatives, metabolites, prodrugs, racemic mixtures or tautomeric forms thereof. To the extent that the free drugs/conjugates include free drugs/conjugates of ionizable paclitaxel, rapamycin, selumetinib, or derivatives thereof, salts such as pharmaceutically acceptable salts may also be used. The examples herein are also presented in order to more fully illustrate the preferred aspects of the present technology. The examples should in no way be construed as limiting the scope of the present technology, as defined by the appended claims. The examples can include or incorporate any of the variations, aspects or aspects of the present technology described above. The variations, aspects or aspects described above may also further each include or incorporate the variations of any or all other variations, aspects or aspects of the present technology.

EXAMPLES

Materials.

All chemicals were purchased from Sigma-Aldrich (St. Louis, Mo.) and used as received. Analytical grade organic solvents and all other reagents were purchased from Fisher Scientific (Pittsburgh, Pa.). PTX was purchased from LC Laboratories (Woburn, Mass.). PEG-b-PLA was purchased from Advanced Polymer Materials Inc. (Montreal, Canada): $M_n$ of PEG and PLA was 4,000 and 2,200 g/mol, respectively; PDI 1.05. A549 human lung adenocarcinoma cells were purchased from ATCC (Manassas, Va.) and grown in RPMI 1640 medium supplemented with 10% fetal bovine serum (FBS), 100 IU/mL penicillin, 100 µg/mL streptomycin, and 2 mM$_L$-glutamine in 5% $CO_2$ incubator at 37° C.

Instrumentation.

Proton nuclear magnetic resonance ($^1$H NMR) data were recorded on a Varian Unity-Inova two-channel 400 MHz NMR spectrometer (Palo Alto, Calif.) with regulated temperature at 25° C. Chemical shifts (δ) were reported in parts per million (ppm) relative to residual protonated solvent resonance at 7.26 ppm for $CDCl_3$. Mass spectrometry data was obtained using the Waters LCT (ESI-TOF) in the Chemical Instrumentation Center in the Department of Chemistry, University of Wisconsin-Madison. Samples were sprayed from a 10 mM $NH_4OAc/CH_3CN$ solution. Reverse-phase HPLC (RP-HPLC) analysis was carried out using a Shimadzu Prominence HPLC system (Shimadzu, Japan) equipped with an LC-20AT pump, a SIL-20AC HT autosampler, a CTO-20AC column oven, and a SPD-M20A diode array detector. Sample was separated by a Waters Symmetry Shield™ RP$_{18}$ column (4.6 mm×250 mm, 5 µm, 100 Å). 10 µL of sample was injected at a flow rate of 0.8 mL/min, column temperature at 25° C., and UV detection wavelength at 227 nm. The separation of o(LA)$_n$-PTX conversion products was done in gradient mode with organic phase containing 100% $CH_3CN$ as solvent A, and aqueous phase containing 100% milliQ water as solvent B. Gradient elution was employed as follows: 0 min, 50% solvent A and 50% solvent B; 35 min, 95% solvent A and 5% solvent B; and 40 min for equilibration. Hydrodynamic diameters of PEG-b-PLA micelles were measured by dynamic light scattering (DLS) using a Zetasizer Nano-ZS (Malvern Instruments Inc., UK)

at 25° C. with a detection angle of 1730 and a He—Ne ion laser as the light source (4 mW, 633 nm). Prior to measurements, PEG-b-PLA micelle solutions were diluted with milliQ water or PBS (10 mM, pH 7.4) to afford the level of PEG-b-PLA at ~0.1 mg/mL and 1 mL of each sample was placed into a disposable sizing cuvette (BRAND Polystyrene Cuvettes). The cumulant method was used to curve-fit the correlation function, and the z-average diameter and polydispersity index (PDI) of PEG-b-PLA micelles were calculated from the Stokes-Einstein equation and the slope of the correlation function, respectively. All measurements were performed in triplicate.

Synthesis of tert-butyldimethylsilyl (TBS)-o(LA)$_n$

Briefly, monodisperse TBS-o(LA)$_8$ and TBS-o(LA)$_{16}$ were synthesized by ring opening of cyclic L-lactide, followed by protection-deprotection to afford monofunctional oligomers, using TBS ether and benzyl ester as protective groups for hydroxyl and carboxylic acid groups, respectively (see Takizawa, K., et al., *J. Polym. Sci. A Polym. Chem.*, 46, 5977-5990 (2008) (incorporated herein by reference)). Selective stepwise ester conjugation of monofunctional oligomers, followed by orthogonal deprotection affords TBS-o(LA)$_8$ and TBS-o(LA)$_{16}$, respectively. $^1$H NMR of TBS-o(LA)$_8$ (400 MHz, CDCl$_3$): δ=5.26-5.05 (m, 7H), 4.40 (q, J=6.6 Hz, 1H), 1.69-1.37 (m, 24H), 0.90 (s, 9H), 0.11 (s, 3H), 0.08 (s, 3H); $^1$H NMR of TBS-LA$_{16}$ (400 MHz, CDCl$_3$): δ=5.23-5.09 (m, 15H), 4.40 (q, J=6.1 Hz, 1H), 1.71-1.34 (m, 48H), 0.90 (s, 9H), 0.11 (s, 3H), 0.08 (s, 3H).

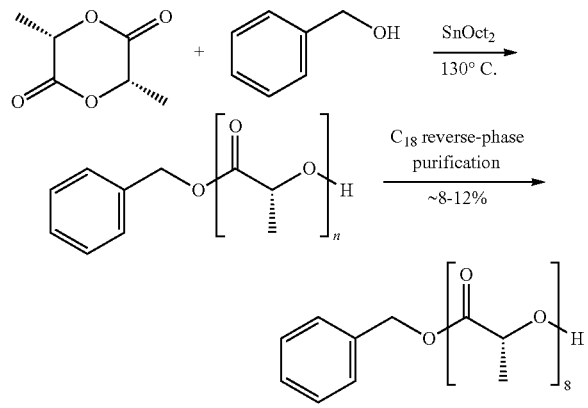

Synthesis of triethylsilyl (TES)-o(LA)$_n$

Briefly, monodisperse TES-o(LA)$_8$ was synthesized by protection-deprotection to afford monofunctional oligomers, using TES ether and benzyl ester as protective groups for hydroxyl and carboxylic acid groups, respectively. Selective stepwise ester conjugation of monofunctional oligomers, followed by orthogonal deprotection affords TES-o(LA)$_8$. (Yield: 99%). $^1$H NMR of TES-o(LA)$_8$ (500 MHz, CDCl$_3$): δ 5.19-5.12 (m, 7H), 4.40 (q, J=7.0 Hz, 6H), 1.59-1.54 (m, 21H), 1.45 (d, J=6.5 Hz, 3H), 0.96 (t, J=7.5 Hz, 9H), 0.62 (q, J=8.0 Hz, 6H).

Synthesis of Benzyl Oligo Lactate, Bn-o(LA)$_n$

Synthesis of polydisperse Bn-o(LA)$_n$ was initiated with tin(II)-ethylhexanoate (Sn(Oct)$_2$). For example, at an average degree of polymerization of 8, cyclic$_L$-lactide was mixed with benzyl alcohol in a molar ratio of 4 to 1. The mixture was stirred at 130° C. until molten. Subsequently, 0.01 w/w % of Sn(Oct)$_2$ in toluene (100 mg/mL) was added. The mixture was stirred at 130° C. for 4 hours and allowed to cool to room temperature, to obtain polydisperse Bn-o(LA)$_n$. Monodisperse Bn-o(LA)$_n$ was purified via a CombiFlash Rf 4× system using C$_{18}$ reverse phase column chromatography. Gradient elution of acetonitrile in 0.1% formic acid and water in 0.1% formic acid was applied. The purified product was concentrated under reduced pressure to provide a colorless liquid. (Yield: ~8-12% for Bn-O(LA)$_8$). $^1$H NMR and MS data are expected to be consistent with the desired product.

Synthesis of 2'-TBS-PTX

2'-TBS-PTX was synthesized as previously reported with slight modification in Forrest, M. L., et al., *Pharm. Res.*, 25, 194-206 (2008); Ali, S., et al., *Anti-Cancer Drugs*, 12, 117-128 (2001) (both incorporated herein by reference). Tert-butyldimethylsilyl chloride (TBSCl) (90 mg, 0.6 mmol) and imidazole (Im) (82 mg, 1.2 mmol) were dissolved into dry DMF (2.0 mL) solution of PTX (250 mg, 0.3 mmol). The reaction mixture was stirred overnight at room temperature under argon. An excess amount of ethyl acetate (40 mL) was poured into the reaction mixture and followed by washing with H$_2$O (1×40 mL) and saturated NH$_4$Cl (1×40 mL) solution. The organic layer was then collected, dried over MgSO$_4$ and filtered. Solvent was removed under reduced pressure and the resulting concentrate was purified via a CombiFlash Rf 4× system (Lincoln, Nebr.) using gradient elution of hexane and ethyl acetate. The purified product was concentrated under reduced pressure to provide a white solid (Yield: 88%). $^1$H NMR (400 MHz, CDCl$_3$): δ=8.27-7.29 (m, 15H), 7.07 (d, J=9.0 Hz, 1H), 6.36-6.20 (m, 2H), 5.74 (d, J=9.0 Hz, 1H), 5.69 (d, J=7.5 Hz, 1H), 4.98 (d, J=9.4 Hz, 1H), 4.66 (s, 1H), 4.43 (d, J=5.5 Hz, 1H), 4.33 (d, J=8.1 Hz, 1H), 4.22 (d, J=8.8 Hz, 1H), 3.83 (d, J=7.5 Hz, 1H), 2.63-2.51 (m, 4H), 2.49-2.35 (m, 2H), 2.23 (s, 3H), 2.13 (dd, J=8.8, 14.9 Hz, 1H), 1.97-1.85 (m, 4H), 1.69 (s, 3H), 1.24 (s, 3H), 1.14 (s, 3H), 0.80 (s, 9H), −0.04 (s, 3H), −0.29 (s, 3H).

Synthesis of 2'-TBS-PTX-o(LA)$_n$-TBS 1,3-dicyclohexylcarbodiimide (DCC) (60 mg, 0.3 mmol) and 4-(dimethylamino)-pyridinium p-toluenesulfonate (DPTS) (15 mg, 0.05 mmol) were added to dry CH$_2$Cl$_2$ (5.0 mL) containing 2'-TBS-PTX (200 mg, 0.2 mmol) and TBS-o(LA)$_8$ (300 mg, 0.2 mmol) or TBS-o(LA)$_{16}$ (420 mg, 0.2 mmol). The reaction mixture was stirred overnight at room temperature under argon. The resulting mixture was filtered and washed with H$_2$O (1×10 mL) and saturated NaHCO$_3$ (1×10 mL) solution. The organic layer was then collected, dried over MgSO$_4$ and filtered. Solvent was removed under reduced pressure and the resulting concentrate was purified via a CombiFlash Rf 4× system using gradient elution of hexane and ethyl acetate. The purified product was concentrated under reduced pressure to provide a white solid (Yield: 20% for 2'-TBS-PTX-o(LA)$_8$-TBS and 24% for 2'-TBS-PTX-o(LA)$_{16}$-TBS). $^1$H NMR of 2'-TBS-PTX-o(LA)$_8$-TBS (400 MHz, CDCl$_3$): δ=8.18-7.28 (m, 15H), 7.08 (d, J=9.2 Hz, 1H), 6.33 (s, 1H), 6.24 (t, J=9.2 Hz, 1H), 5.79-5.68 (m, 2H), 5.64-5.53 (m, 1H), 5.24-5.06 (m, 7H), 4.95 (d, J=9.4 Hz, 1H), 4.66 (s, 1H), 4.44-4.36 (m, 1H), 4.34 (d, J=8.8 Hz, 1H), 4.21 (d, J=8.4 Hz, 1H), 3.96 (d, J=6.6 Hz, 1H), 2.68-2.54 (m, 4H), 2.42 (dd, J=9.8, 15.1 Hz, 1H), 2.21-2.10 (m, 4H), 1.97 (s, 3H), 1.93-1.84 (m, 1H), 1.82 (br, 3H), 1.67-1.39 (m, 24H), 1.19 (s, 3H), 1.16 (s, 3H), 0.90 (s, 9H), 0.80 (s, 9H), 0.10 (s, 3H), 0.08 (s, 3H), −0.03 (s, 3H), −0.30 (s, 3H); $^1$H NMR of 2'-TBS-PTX-o(LA)$_{16}$-TBS (400 MHz, CDCl$_3$): δ=8.16-7.28 (m, 15H), 7.10-7.05 (m, 1H), 6.33 (s, 1H), 6.29-6.19 (m, 1H), 5.72 (s, 2H), 5.65-5.55 (m, 1H), 5.23-5.06 (m, 15H), 4.99-4.90 (m, 1H), 4.66 (d, J=1.6 Hz, 1H), 4.43-4.36 (m, 1H), 4.36-4.31 (m, 1H), 4.26-4.18 (m, 1H), 3.99-3.91 (m, 1H), 2.57 (s, 4H), 2.48-2.35 (m, 1H), 2.19-2.09 (m, 4H), 1.97 (s, 3H), 1.93-1.83 (m, 1H), 1.81 (s, 3H), 1.67-1.37 (m, 48H), 1.19 (s, 3H), 1.15 (s, 3H), 0.90 (s, 3H), 0.79 (s, 9H), 0.10 (s, 2H), 0.08 (s, 2H), −0.03 (s, 3H), −0.30 (s, 3H).

Synthesis of o(LA)$_n$-PTX Conjugate

To a solution of 2'-TBS-PTX-o(LA)$_8$-TBS (85 mg, 0.06 mmol) or 2'-TBS-PTX-o(LA)$_{16}$-TBS (120 mg, 0.06 mmol) in dry THF (2 mL), acetic acid (72 mg, 1.2 mmol) and tetrabutylammonium fluoride (TBAF) (1.0 M THF solution) (63 mg, 0.24 mmol) were gradually added. The reaction mixture was stirred overnight at room temperature under argon. Excess amount of ethyl acetate (40 mL) was poured into the reaction mixture and washed with saturated NaHCO$_3$ (2×40 mL) solution, 5 wt % aqueous citric acid (2×40 mL), and H$_2$O (1×40 mL). The organic layer was then collected, dried over MgSO$_4$ and filtered. Solvent was removed under reduced pressure, and the resulting concentrate was purified via a CombiFlash Rf 4× system using gradient elution of hexane and ethyl acetate. The purified product was concentrated under reduced pressure to provide a white solid (Yield: 70% for o(LA)$_8$-PTX and 72% for o(LA)$_{16}$-PTX). $^1$H NMR of o(LA)$_8$-PTX (400 MHz, CDCl$_3$): δ=8.17-7.31 (m, 15H), 7.01 (d, J=8.9 Hz, 1H), 6.29 (s, 1H), 6.23-6.13 (m, 1H), 5.85-5.75 (m, 1H), 5.68 (d, J=7.0 Hz, 1H), 5.62-5.47 (m, 1H), 5.33-5.02 (m, 7H), 4.91 (d, J=8.5 Hz, 1H), 4.79 (dd, J=2.5, 4.9 Hz, 1H), 4.38-4.33 (m, 1H), 4.32 (d, J=8.3 Hz, 1H), 4.19 (d, J=7.8 Hz, 1H), 3.92 (d, J=6.8 Hz, 1H), 3.54 (d, J=4.9 Hz, 1H), 2.67-2.55 (m, 2H), 2.38 (s, 3H), 2.33 (d, J=8.1 Hz, 1H), 2.15 (s, 3H), 1.84 (s, 4H), 1.81 (s, 3H), 1.64-1.46 (m, 24H), 1.20 (s, 3H), 1.16 (s, 3H). ESI-TOF: m/z calcd for C$_{71}$H$_{83}$NO$_{30}$ [M+NH$_4$]$^+$: 1447.5; found 1447.2. $^1$H NMR of o(LA)$_{16}$-PTX (400 MHz, CDCl$_3$): δ=8.21-7.30 (m, 15H), 7.09-6.95 (m, 1H), 6.29 (s, 1H), 6.23-6.11 (m, 1H), 5.84-5.75 (m, 1H), 5.73-5.65 (m, 1H), 5.61-5.49 (m, 1H), 5.33-5.04 (m, 15H), 4.91 (d, J=9.4 Hz, 1H), 4.84-4.74 (m, 1H), 4.40-4.33 (m, 1H), 4.33-4.29 (m, 1H), 4.23-4.16 (m, 1H), 3.92 (d, J=6.6 Hz, 1H), 3.55 (d, J=5.3 Hz, 1H), 2.71-2.53 (m, 2H), 2.38 (s, 3H), 2.33 (d, J=8.0 Hz, 1H), 2.15 (s, 3H), 1.84 (s, 4H), 1.81 (s, 3H), 1.66-1.45 (m, 48H), 1.20 (s, 3H), 1.16 (s, 3H). ESI-TOF: m/z calcd C$_{95}$H$_{115}$NO$_{46}$ [M+Na]$^+$: 2029.3; found 2029.4.

Synthesis of o(LA)$_n$-RAP-TES Conjugate 1,3-dicyclohexylcarbodiimide (DCC) (100 mg, 0.49 mmol) and 4-dimethylaminopyridine (DMAP) (12 mg, 0.10 mmol) were added to dry CH$_2$Cl$_2$ (5 mL) containing RAP (298 mg, 0.33 mmol) and TES-o(LA)$_8$ (254 mg, 0.36 mmol). The reaction mixture was stirred overnight at room temperature under argon and determined to be complete by TLC. The resulting mixture was concentrated under reduced pressure and the residue was purified via a CombiFlash Rf 4× system using gradient elution of hexane and ethyl acetate. The purified product was concentrated under reduced pressure to provide RAP-o(LA)$_8$-TES (296 mg, Yield: 57%). $^1$H NMR of RAP-40-o(LA)$_8$-TES (500 MHz, CDCl$_3$, major rotamer): δ 6.38 (dd, J=10.5, 15.0 Hz, 1H), 6.30 (dd, J=10.0, 15.0 Hz, 1H), 6.14 (dd, J=10.0, 15.0 Hz, 1H), 5.96 (d, J=11.0 Hz, 1H), 5.54 (dd, J=9.0, 15.0 Hz, 1H), 5.41 (d, J=9.5 Hz, 1H), 5.28 (d, J=6.0 Hz, 1H), 5.19-5.11 (m, 8H), 4.77 (s, 1H), 4.71 (ddd, J=5.0, 9.5, 11.5 Hz, 1H), 4.40 (q, J=6.5 Hz, 1H), 4.17 (d, J=6.0 Hz, 1H), 3.74 (d, J=6.0 Hz, 1H), 3.57 (d, J=14.0 Hz, 1H), 3.37 (s, 3H), 3.33 (s, 3H), 3.14 (s, 3H), 2.71 (dd, J=6.0, 17.0 Hz, 1H), 1.51 (d, J=7.0 Hz, 3H), 1.50 (d, J=7.0 Hz, 3H), 1.09 (d, J=6.5 Hz, 3H), 1.05 (d, J=6.5 Hz, 3H), 0.99-0.94 (m, 15H), 0.90 (d, J=7.0 Hz, 3H), 0.63 (q, J=8.0 Hz, 6H).

Synthesis of o(LA)$_n$-RAP Conjugate

To a solution of RAP-o(LA)$_8$-TES (272 mg, 0.17 mmol) in THF (9 mL) was added pyridine (0.41 mL, 5.08 mmol) and HF/Pyr (0.13 mL, 5.08 mmol, 70% HF) successively. The reaction mixture was stirred 1 h at room temperature under argon and then quenched with saturated aqueous NaHCO$_3$ solution. The mixture was extracted with EtOAc (3×40 mL) and the combined organic phases were washed with brine, dried with anhydrous Na$_2$SO$_4$, filtered and the filtrate was concentrated under reduced pressure to afford a crude mixture which was purified via a CombiFlash Rf 4× system using gradient elution of hexane and ethyl acetate to afford pure o(LA)$_8$-RAP conjugate as a white solid (219 mg, 87%). $^1$H NMR of o(LA)$_8$-RAP (500 MHz, CDCl$_3$, major rotamer): δ 6.38 (dd, J=10.5, 14.5 Hz, 1H), 6.31 (dd, J=10.0, 15.0 Hz, 1H), 6.14 (dd, J=10.0, 15.0 Hz, 1H), 5.96 (d, J=11.0 Hz, 1H), 5.54 (dd, J=9.0, 15.0 Hz, 1H), 5.41 (d, J=9.5 Hz, 1H), 5.28 (d, J=6.5 Hz, 1H), 5.24-5.11 (m, 8H), 4.77 (s, 1H), 4.71 (ddd, J=5.0, 9.0, 11.5 Hz, 1H), 4.18 (d, J=6.0 Hz, 1H), 3.74 (d, J=5.5 Hz, 1H), 3.67 (q, J=7.0 Hz, 1H), 3.57 (d, J=20.5 Hz), 3.37 (s, 3H), 3.33 (s, 3H), 3.14 (s, 3H), 2.71 (dd, J=5.5, 17.0 Hz, 1H), 2.66 (d, J=6.0 Hz, 1H), 2.57 (dd, J=5.5, 17.0 Hz, 1H), 1.09 (d, J=6.5 Hz, 3H), 1.05 (d, J=7.0 Hz, 3H), 0.99 (d, J=6.5 Hz, 3H), 0.95 (d, J=6.5 Hz, 3H), 0.90 (d, J=7.0 Hz, 3H).

Synthesis of o(LA)$_n$-SEL Conjugate

To a solution of SEL (153 mg, 0.33 mmol) and TES-o(LA)$_8$ (260 mg, 0.38 mmol) in DMF (3.3 mL) was added HOBT (75 mg, 0.50 mmol), DCC (103 mg, 0.50 mmol) and DMAP (12 mg, 0.10 mmol) successively at room temperature under argon. The reaction was concentrated under reduced pressure after stirring overnight to afford a crude mixture which was further purified via a CombiFlash Rf 4× system using gradient elution of hexane and ethyl acetate to afford pure o(LA)$_8$-SEL conjugate (176 mg, 51%). $^1$H NMR of o(LA)$_8$-SEL (500 MHz, CDCl$_3$): δ 10.25 (s, 1H), 7.99 (s, 1H), 7.93 (s, 1H), 7.52 (d, J=2.0 Hz, 1H), 7.14 (dd, J=2.0, 9.0 Hz, 1H), 6.65 (s, 1H), 6.36 (dd, J=2.0, 9.0 Hz, 1H), 5.24-5.09 (m, 7H), 4.38-4.31 (m, 2H), 4.23-4.19 (m, 1H), 4.07-4.06 (m, 2H), 3.93 (s, 3H), 2.70 (d, J=6.0 Hz, 1H), 1.60-1.48 (m, 24H). HRMS (QTOF MS ESI) m/e calcd for C$_{41}$H$_{48}$BrClFN$_4$O$_{19}$ [M+H]$^+$1035.1749, found 1035.1758.

Reductive Degradation of o(LA)$_8$-PTX Conjugate.

Reductive degradation of o(LA)$_8$-PTX at the C-13 position was achieved as previously reported in Magri, N. F., et al., *J. Org. Chem.*, 51, 3239-3242 (1986) (incorporated herein by reference). In brief, o(LA)$_8$-PTX (10 mg, 7 μmol) or PTX (6 mg, 7 μmol) in dry CH$_2$Cl$_2$ (2 mL) was treated with Bu$_4$NBH$_4$ (1.2 mg, 14 μmol) for 2 h under argon. One drop of acetic acid was added to terminate the reaction followed by solvent removal under vacuum. The residual solid was redissolved in $CH_3CN$ and analyzed by RP-HPLC. Desired fractions of (1S, 2R)—N-(2,3-dihydroxy-1-phenylpropyl)-benzamide (DPPB) and o-$LA_8$ conjugated baccatin III ($OLA_8Bac$) were collected from degradation products of o$(LA)_8$-PTX and analyzed by mass spectrometry. Results were consistent with coupling of o$(LA)_8$ solely at the 7-OH position of PTX. ESI-TOF of DPPB: m/z calcd for $C_{16}H_{17}NO_3$ [M+Na]$^+$: 294.1; found 294.1. ESI-TOF of o$(LA)_8Bac$: m/z calcd for $C_{55}H_{70}O_{27}$ [M+NH$_4$]$^+$: 1180.4; found 1180.6.

Preparation and Characterization of PEG-b-PLA Micelles Containing PTX, o$(LA)_8$-PTX and o$(LA)_{16}$-PTX.

PTX, o$(LA)_8$-PTX or o$(LA)_{16}$-PTX was loaded into PEG-b-PLA micelles using a thin-film hydration method as previously reported in Shin, H., et al., *Mol. Pharm.*, 8, 1257-1265 (2011) (incorporated herein by reference). Briefly, PTX, o$(LA)_8$-PTX or o$(LA)_{16}$-PTX (1.0 mg) and PEG-b-PLA (10.0 mg) were dissolved in 1.0 mL of $CH_3CN$ in a round-bottom flask; $CH_3CN$ was removed by reduced pressure using a rotary evaporator at 60° C. to attain a dried thin film. The polymeric film was dissolved by addition of sterile water or PBS (10 mM, pH 7.4), followed by centrifugation for 5 min at 13,000 rpm and sterile filtration (0.22 µm (Coring, N.Y.)). Aqueous solubility, drug loading efficiency, and drug loading content of PTX, o$(LA)_8$-PTX or o$(LA)_{16}$-PTX were quantified by RP-HPLC. Drug loading efficiency was calculated by dividing the level of PTX, o$(LA)_8$-PTX or o$(LA)_{16}$-PTX loaded in PEG-b-PLA micelles by the initial drug or conjugate level used for drug loading. Drug loading content was calculated based on the weight of PTX, o$(LA)_8$-PTX or o$(LA)_{16}$-PTX divided by the total weight of PTX, o$(LA)_8$-PTX or o$(LA)_{16}$-PTX plus PEG-b-PLA micelles. Similarly, the PEG-b-PLA micelles containing RAP, o$(LA)_8$-RAP, SEL, or o$(LA)_8$-SEL were prepared and characterized.

Conversion of o$(LA)_8$-PTX or o$(LA)_{16}$-PTX Conjugates in an $CH_3CN$/PBS Mixture and in PEG-b-PLA Micelles in PBS.

Conversion of o$(LA)_8$-PTX or o$(LA)_{16}$-PTX in a (1:1) mixture of $CH_3CN$ and PBS (10 mM, pH 7.4) was analyzed by RP-HPLC. Solutions of o$(LA)_8$-PTX or o$(LA)_{16}$-PTX (1.0 mg/mL) were placed in a 1.5 mL Eppendorf tube and incubated at 37° C. in a temperature adjusted water-bath (GCA Corporation, IL). 20 µL solution was drawn at predetermined time points, and diluted by 180 µL of $CH_3CN$. Similarly, conversion of o$(LA)_8$-PTX or o$(LA)_{16}$-PTX in PEG-b-PLA micelles (1.0 mg/mL in water) was measured. 20 µL solution was drawn at predetermined time points, centrifuged, filtered (0.22 m) and diluted by 180 µL of $CH_3CN$. RP-HPLC analysis was done immediately after sample preparation. First-order constants were calculated for the degradation kinetics of o$(LA)_8$-PTX or o$(LA)_{16}$-PTX. The conversion of o$(LA)_8$-PTX or o$(LA)_{16}$-PTX was evaluated at least three times with standard deviation. Similarly, the conversion of o$(LA)_8$-RAP and o$(LA)_8$-SEL was conducted.

In Vitro Release Studies.

After loading of PTX, o$(LA)_8$-PTX or o$(LA)_{16}$-PTX conjugate into PEG-b-PLA micelles, samples were diluted to 0.5 mg/mL using PBS solution (10 mM, pH 7.4), and 2.5 mL of diluted micelle solution was loaded into a Slide-A-Lyzer™ Dialysis Cassette with MWCO 20K (Thermo Scientific, MA). Four dialysis cassettes were placed in 4 L PBS solution (10 mM, pH 7.4) on a Corning Hotplate Stirrer (Corning, N.Y.) at 37° C. The sampling time intervals were 0, 0.5, 1, 2, 4, 8, 12, 24, 48 and 72 h. At each time point, a sample of 100 µL was withdrawn, and the cassettes were replenished with 100 µL of fresh PBS solution (10 mM, pH 7.4). The external medium was replaced with 4 L of fresh buffer at 2, 4, 8, 12, 24 and 48 h to approximate sink conditions. The quantity of PTX, o$(LA)_8$-PTX or o$(LA)_{16}$-PTX remaining in PEG-b-PLA micelles was determined by RP-HPLC analysis, and percent drug release was calculated over time along with first-order rate constants.

In Vitro Cytotoxicity Studies.

The cytotoxicity of PTX, o$(LA)_8$-PTX or o$(LA)_{16}$-PTX (free and micelle-associated) against an A549 non-small lung carcinoma cell lines was investigated by the CellTiter-Blue® Cell Viability Assay (Promega, Wis.). The cells were seeded into a 96-well plate at a seeding density of 1,500 cells/100 µL/well and cultured in RPMI 1640 medium at 37° C. in 5% $CO_2$ incubator for 24 h. PTX, o$(LA)_2$-PTX or o$(LA)_8$-PTX was dissolved in DMSO, whereas PTX, o$(LA)_8$-PTX or o$(LA)_{16}$-PTX containing PEG-b-PLA micelles were in a PBS solution (10 mM, pH 7.4). Each was added into the wells to attain a final concentrations of 0.1, 1, 10, 100, and 1000 nM. The final level of DMSO in the medium was <0.1% at all drug levels. Cells cultured with diluted DMSO or PBS in medium were used as controls. Drug treated cells were placed in an incubator at 5% $CO_2$ at 37° C. for 72 h. The medium in each well was aspirated, and 100 µL of 20% (v/v) CellTiter-Blue reagent in serum free RPMI medium was added, followed by incubation at 37° C. in 5% $CO_2$ atmosphere for 1.5 h. Fluorescence intensity was measured by a SpectraMax M2 plate reader (Molecular Devices, CA) with excitation and emission at 560 and 590 nm, respectively. The half maximal inhibitory drug concentration ($IC_{50}$) was determined by using GraphPad Prism version 5.00 for Windows (GraphPad Software, CA). Similarly, the cytotoxicity of RAP, o$(LA)_8$-RAP, SEL, and o$(LA)_8$-SEL (free and micelle-associated) against an A549 non-small lung carcinoma cell lines were investigated.

In Vivo Antitumor Efficacy.

All animal experiments were conducted under the protocol approved by Institutional Animal Care and Use Committee in University of Wisconsin-Madison in accordance with institutional and NIH guidance for the Care and Use of Laboratory Animals. 6-8 week-old female athymic nude mice (20-25 g each) were acquired from laboratory animal resources at School of Medicine and Public Health, University of Wisconsin-Madison. Mice were housed in ventilated cages with free access to water and food and acclimated for 1 week prior tumor cell injection. A549 cells ($2 \times 10^6$ cells in 100 µL of serum-free RPMI 1640 medium) were harvested from sub-confluent cultures after trypsinization and were injected subcutaneously into the right flank of each mouse. When tumor volume had reached approximately 150 mm$^3$, mice were randomly divided into 3 treatment groups (n=3-4/group): PTX loaded PEG-b-PLA micelles at 20 mg/kg, o$(LA)_8$-PTX-loaded PEG-b-PLA micelles at 20 mg/kg PTX equivalents, and empty PEG-b-PLA micelles. Drug conjugates were administered via tail vein for 3 weekly injections, followed by 1-week rest period, totaling 3 cycles over a 12 weeks period. Body weight and tumor volume were monitored over the course of study. Tumor volume was calculated using the formula: $V=(a \times b^2)/2$, where V is tumor volume, a is tumor length, b is tumor width.

Data Analysis.

Student's t-test at 5% significance level or one-way ANOVA at 5% significance level were performed for statistical analysis. All data analyses were performed using GraphPad Prism version 5.00 for Windows (GraphPad Software, CA).

Results.

Characterization of PEG-b-PLA Micelles Containing PTX, RAP, SEL, and o(LA)n-Conjugates Thereof.

Physicochemical properties of PEG-b-PLA micelles containing PTX, o(LA)$_8$-PTX conjugate, or o(LA)$_{16}$-PTX conjugate are summarized in Table 1A. Physicochemical properties of PEG-b-PLA micelles containing RAP or o(LA)$_8$-RAP conjugate are summarized in Table 1B. Physicochemical properties of PEG-b-PLA micelles containing SEL or o(LA)$_8$-SEL conjugate are summarized in Table 1C.

TABLE 1A

Physicochemical properties of PEG-b-PLA micelles containing PTX, o(LA)$_8$-PTX or o(LA)$_{16}$-PTX conjugate.

| Drug | Initial level of PTX (mg)[a] | Drug to polymer ratio | Particle Size (nm) | Drug loading efficiency (%) | Drug loading (%) | Apparent solubility (mg/mL) | Stability (h) |
|---|---|---|---|---|---|---|---|
| PTX | 1 | 1:10 | 30.5 ± 0.3 | 93.8 ± 12.8 | 8.6 ± 1.1 | 0.9 ± 0.1 | <2 |
|  | 6 | 3:5 | 37.0 ± 5.7 | 21.0 ± 2.3 | 11.2 ± 1.1 | 1.2 ± 0.1 | <2 |
| o(LA)$_8$-PTX | 1 | 1:10 | 32.7 ± 0.6 | 94.9 ± 3.6 | 8.7 ± 0.4 | 0.9 ± 0.4 | >72 |
|  | 6 | 3:5 | 58.8 ± 0.3 | 98.4 ± 10.0 | 37.1 ± 2.3 | 5.9 ± 0.6 | >72 |
|  | 12 | 1.2:1 | 100.0 ± 1.3 | 100.7 ± 10.0 | 54.5 ± 4.3 | 12 ± 1.0 | >72 |
| o(LA)$_{16}$-PTX | 1 | 1:10 | 31.0 ± 0.2 | 96.4 ± 3.3 | 8.8 ± 0.3 | 1.0 ± 0.3 | >72 |
|  | 6 | 3:5 | 87.7 ± 0.8 | 104 ± 5.0 | 38.6 ± 1.0 | 6.2 ± 0.2 | >72 |
|  | 12 | 1.2:1 | 89.0 ± 6.3 | 45.8 ± 3.6 | 35.4 ± 1.8 | 5.5 ± 0.4 | >72 |

[a]10 mg of PEG-b-PLA was used in each formulation. (mean ± SD, n = 3)

PEG-b-PLA micelles increased the water solubility of PTX from ca. 10 mg/L to 0.9 mg/mL, forming micelles with an average hydrodynamic diameter at 30.5 nm and 8.6% drug loading. However, an increase in the water solubility of PTX was not realized by a 6-fold increase in the initial level of PTX used in drug loading. Instead, loading efficiency of PTX was low, ca. 21%, and drug loading for PEG-b-PLA micelles leveled off at 11.2% drug loading. Notably, PEG-b-PLA micelles containing PTX were unstable at room temperature, precipitating in less than 2 hours. By contrast, drug loading of o(LA)$_8$-PTX conjugate for PEG-b-PLA micelles increased from 8.7 to 37.1 and 54.5% with a 6- and 12-fold increase in the initial level of conjugate, respectively, and loading efficiency was ca. 100%. The hydrodynamic diameter of PEG-b-PLA micelles containing o(LA)$_8$-PTX conjugate at 37.1% and 54.5%, increased to 58.8 nm and 100 nm, respectively. Drug loading of o(LA)$_{16}$-PTX conjugate was also higher than PTX for PEG-b-PLA micelles, ca. 39% and 6.2 mg/mL in water. Notably, PEG-b-PLA micelles containing o(LA)$_8$-PTX or o(LA)$_{16}$-PTX conjugate were stable at 37° C. for more than 72 hours, indicating thermodynamic stability for o(LA)$_8$-PTX or o(LA)$_{16}$-PTX conjugate solubilization. At 9% drug loading and particle size at 30 nm, PEG-b-PLA micelles rapidly released PTX in vitro, resulting in precipitation of PTX<4 hours (FIG. 4). By contrast, in vitro release of o(LA)$_8$-PTX or o(LA)$_{16}$-PTX conjugate from PEG-b-PLA micelles (FIG. 4) was gradual, with $t_{1/2}$=14.2 and 26.5 hours, respectively, indicating control of conjugate release by tuning of o(LA)$_n$ chain length. These results show that oligolactic acid acts as a compatibilizer between the present conjugates and PEG-b-PLA micelles, resulting in improvements in drug loading, physical stability and drug release in comparison to PTX.

TABLE 1B

Physicochemical properties of PEG-b-PLA micelles containing RAP or o(LA)$_8$-RAP conjugate.

| Drug | Drug to polymer ratio | Particle size (nm) | Drug loading efficiency (%) | Drug loading (%) | Apparent solubility (mg/mL) | Stability (h) |
|---|---|---|---|---|---|---|
| o(LA)$_8$-RAP | 1:10 | 35.9 ± 0.3 | 80.4 | 7.3 | 1.6 | >24 |
|  | 1:5 | 60.8 ± 0.4 | 81.5 | 13.6 | 1.6 | >24 |
|  | 1:1 | 96.1 ± 5.7 | 87.8 | 43.9 | 1.7 | <24 |
| RAP | 1:10 | 37.7 ± 1.9 | 70.1 | 6.4 | 1.4 | <24 |
|  | 1:5 | 36.2 ± 0.4 | 44.0 | 7.3 | 0.9 | <24 |
|  | 1:1 | 59.5 ± 21.6 | 23.0 | 11.5 | 0.5 | <24 |

RAP drug loading for PEG-b-PLA micelles was 6.4% and leveled off at 11.5% drug loading with a low drug loading efficiency of 23%. By contrast, drug loading of o(LA)$_8$-RAP conjugate for PEG-b-PLA micelles was higher and increased from 7.3 to 13.6 and 43.9% and a loading efficiency of greater than 80%. The hydrodynamic diameter of PEG-b-PLA micelles containing o(LA)$_8$-RAP conjugate at 13.6% and 43.9%, increased to 60.8 nm and 96 nm, respectively. Notably, PEG-b-PLA micelles containing 7.3% and 13.6% o(LA)$_8$-RAP were stable at 37° C. for more than 24 hours, indicating thermodynamic stability for o(LA)$_8$-RAP conjugate solubilization in vitro. In contrast, all of the PEG-b-PLA micelles containing unconjugated RAP released RAP in less than 24 hours. These results show that oligolactic acid acts as a compatibilizer between the present conjugates and PEG-b-PLA micelles, resulting in improvements in drug loading and physical stability in comparison to RAP.

TABLE 1C

Physicochemical properties of PEG-b-PLA micelles containing SEL or o(LA)$_8$-SEL conjugate.

| Drug | Drug to polymer ratio | Particle size (nm) | Drug loading efficiency (%) | Drug loading (%) | Apparent solubility (mg/mL) | Stability (h) |
|---|---|---|---|---|---|---|
| o(LA)$_8$-SEL | 1:10 | 39.6 ± 5.3 | 43.5 | 4.1 | 0.9 | >24 |
|  | 1:5 | 126.3 ± 2.2 | 54.8 | 9.9 | 1.1 | <2 |
|  | 1:1 | 101.1 ± 2.3 | 30.7 | 23.5 | 0.6 | <2 |
| SEL | 1:5 | 60.6 ± 0.6 | 5.1 | 1 | 0.1 | <2 |

SEL drug loading for PEG-b-PLA micelles was 1% with a very low drug loading efficiency of 5%. By contrast, drug loading of o(LA)$_8$-SEL conjugate for PEG-b-PLA micelles was higher and increased from 4.1 to 9.9 and 23.5% and a loading efficiency of greater than 30%. The hydrodynamic diameter of PEG-b-PLA micelles containing o(LA)$_8$-SEL conjugate at 9.9% and 2.5%, increased to 126 nm and 101 nm, respectively. Notably, PEG-b-PLA micelles containing 4.1% o(LA)$_8$-RAP were stable at 37° C. for more than 24 hours, indicating thermodynamic stability for o(LA)$_8$-SEL conjugate solubilization in vitro. In contrast, the PEG-b-PLA micelles containing unconjugated SEL were unstable and SEL precipitated out within about 5 minutes. These results show that oligolactic acid acts as a compatibilizer between the present conjugates and PEG-b-PLA micelles, resulting in improvements in drug loading and physical stability in comparison to SEL.

Characterization of PEG-b-PLA Micelles Containing the 3-Drug Combination of Unconjugated PTX, SEL, and RAP.

Physicochemical properties of PEG-b-PLA micelles containing PTX, SEL, and RAP as a 3-in-1 micelle are summarized in Table 2. As provided in Table 1C, SEL drug loading for PEG-b-PLA micelles was very low at 1% with low drug loading efficiency of 5%. Additionally, the PEG-b-PLA micelles containing unconjugated SEL were unstable and SEL precipitated out within about 5 minutes. In contrast, SEL was successfully loaded at 6.3% in PEG-b-PLA micelles when co-loaded with PTX and RAP. Surprisingly, when co-loaded, PTX, RAP, and SEL all achieved a drug loading efficiency of 100%. These results show that co-loading of the 3-drug combination with PEG-b-PLA micelles provides improvements in drug loading and physical stability compared to individual drug loading in PEG-b-PLA micelles.

TABLE 2

Physicochemical properties of PEG-b-PLA micelles containing PTX, SEL, and RAP as a 3-in-1 micelle.

| | Initial level (mg)[a] | Molar ratio | Loading efficiency (%) | Drug loading (%) | Total drug loading (%) | Size (nm) |
|---|---|---|---|---|---|---|
| PTX | 1 | 2 | 104 | 4.3 | 12.8 | 28.9 |
| SEL | 1.5 | 6 | 101.7 | 6.3 | | |
| RAP | 0.5 | 1 | 104.6 | 2.2 | | |

[a]21 mg of PEG$_{4000}$-b-PLA$_{2200}$ polymer was used.

Conversion of o(LA)$_8$-PTX, o(LA)$_{16}$-PTX, o(LA)$_8$-RAP, and o(LA)$_8$-SEL Conjugates.

Figure 2A:
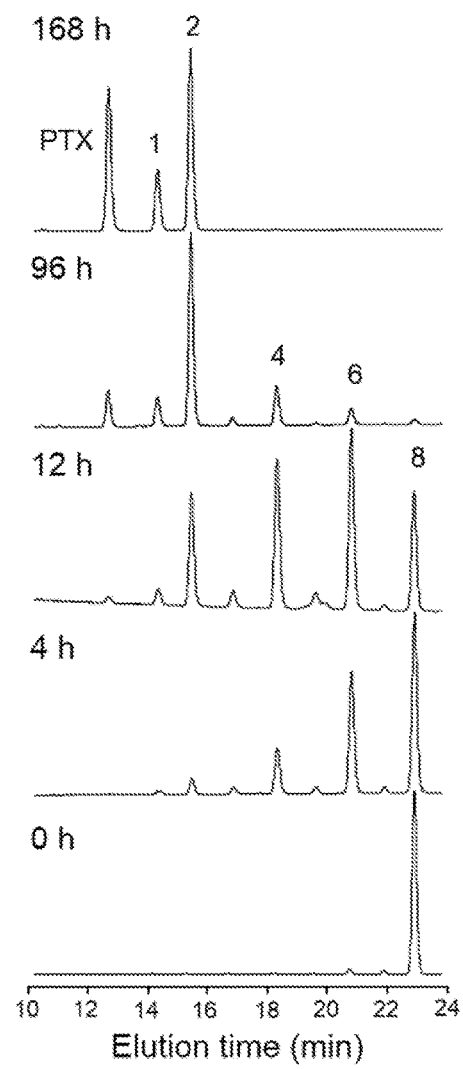
FIGS. 2A and 2B show reverse-phase HPLC chromatograms of o(LA)$_8$-PTX conjugate (2A) and o(LA)$_{16}$-PTX conjugate (2B) and their backbiting conversion products after incubation in 1:1 CH$_3$CN/10 mM PBS at 37° C., pH 7.4 at 0, 4, 12, 96 and 168 hours.
Figure 2B:
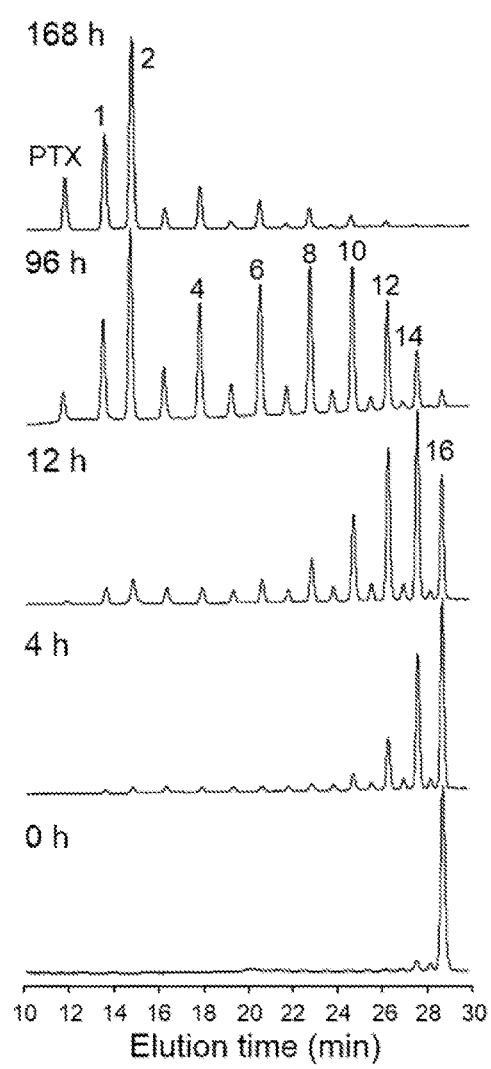
Figure 5A:
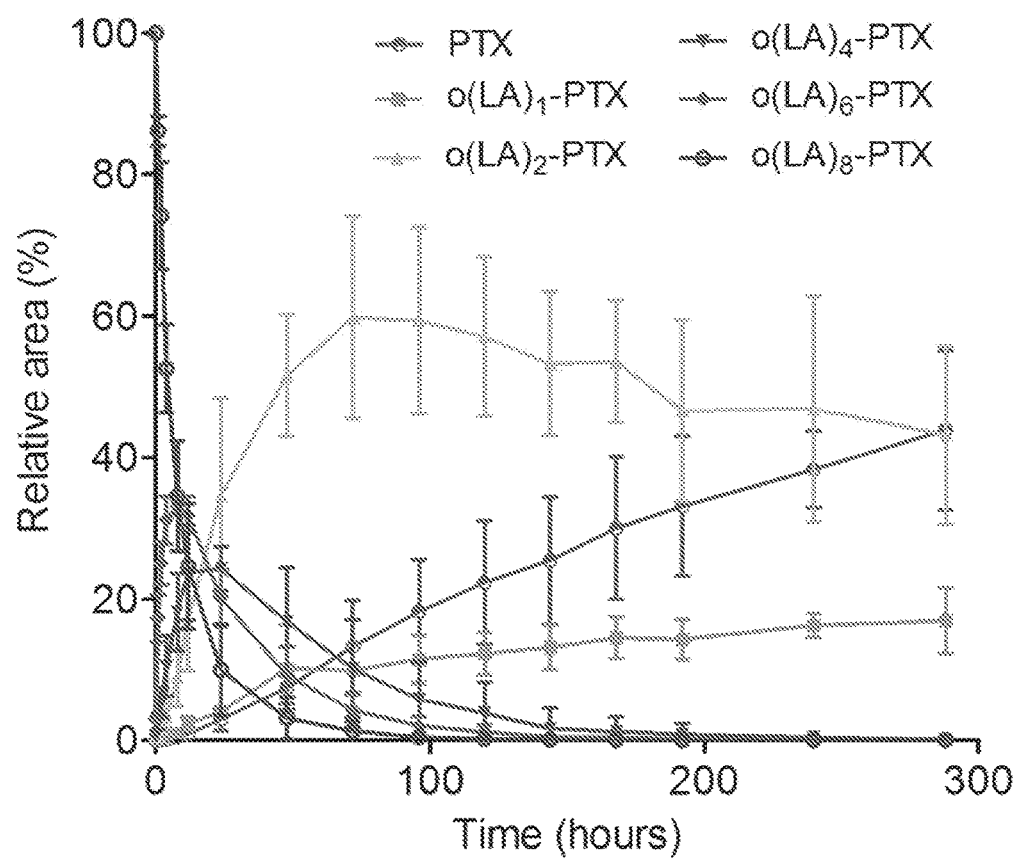
FIGS. 5A and 5B show respectively, a graph showing the time course of the conversion of o(LA)$_8$-PTX conjugate into o(LA)$_6$-PTX, o(LA)$_4$-PTX, o(LA)$_2$-PTX, o(LA)$_1$-PTX and PTX (mean±SD, n=3) (5A) and a graph showing the time course of the conversion of o(LA)$_{16}$-PTX conjugate into o(LA)$_{14}$-PTX, o(LA)$_{12}$-PTX, o(LA)$_{10}$-PTX, o(LA)$_8$-PTX, o(LA)$_6$-PTX, o(LA)$_4$-PTX, o(LA)$_2$-PTX, o(LA)$_1$-PTX and PTX (mean±SD, n=3) (5B).
Figure 5B:
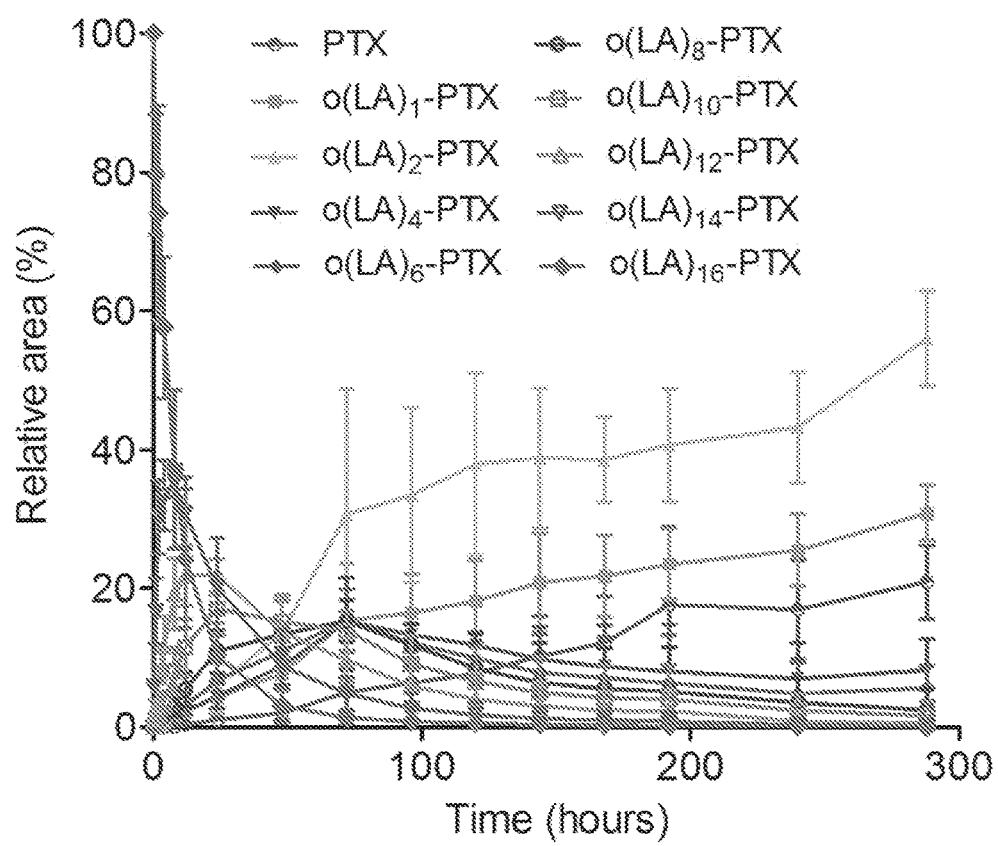
Figure 7A:
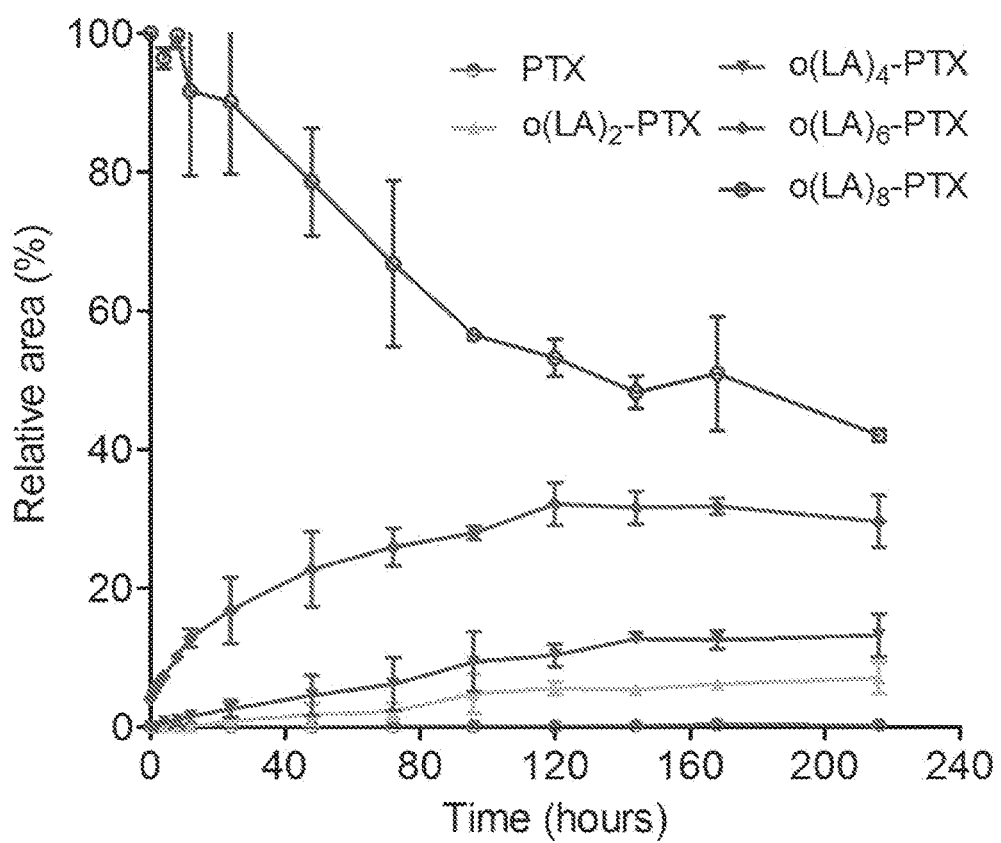
FIG. 7A shows the time course of the conversion of o(LA)$_8$-PTX conjugate in PEG-b-PLA micelles into o(LA)$_6$-PTX, o(LA)$_4$-PTX, o(LA)$_2$-PTX and PTX (mean±SD, n=3).
Figure 7B:
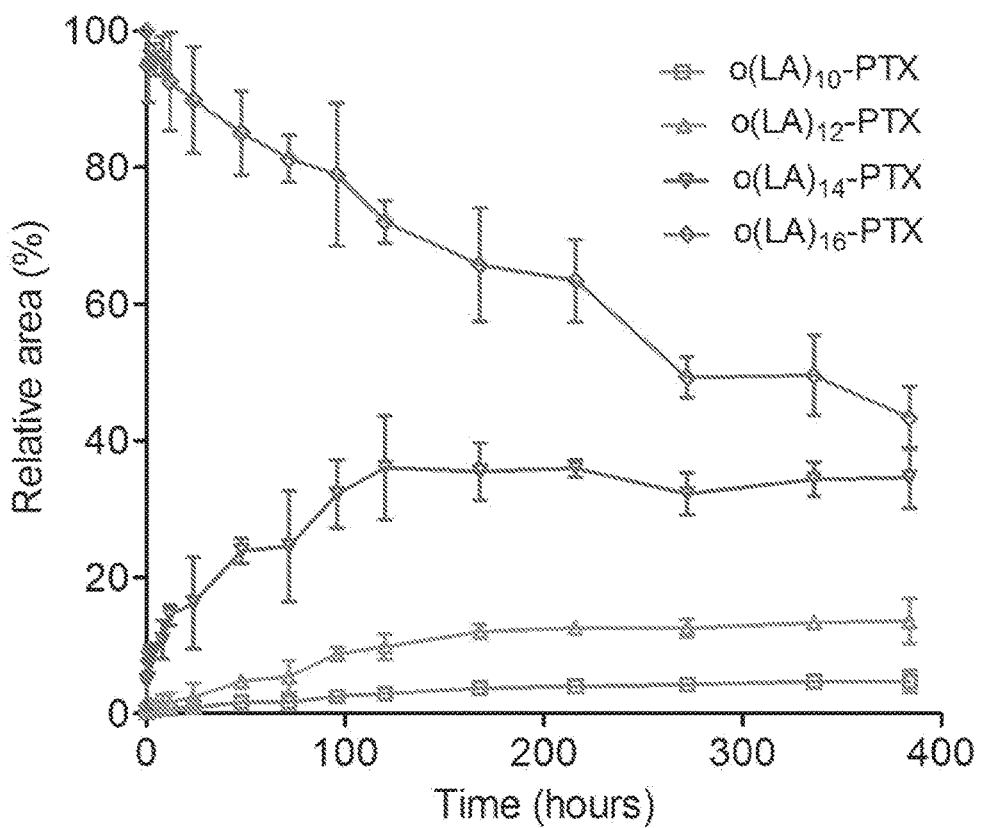
FIG. 7B shows the time course of the conversion of o(LA)$_{16}$-PTX conjugate in PEG-b-PLA micelles into o(LA)$_{14}$-PTX, o(LA)$_4$-PTX, o(LA)$_{12}$-PTX and o(LA)$_{10}$-PTX (mean±SD, n=3).
Figure 10A:
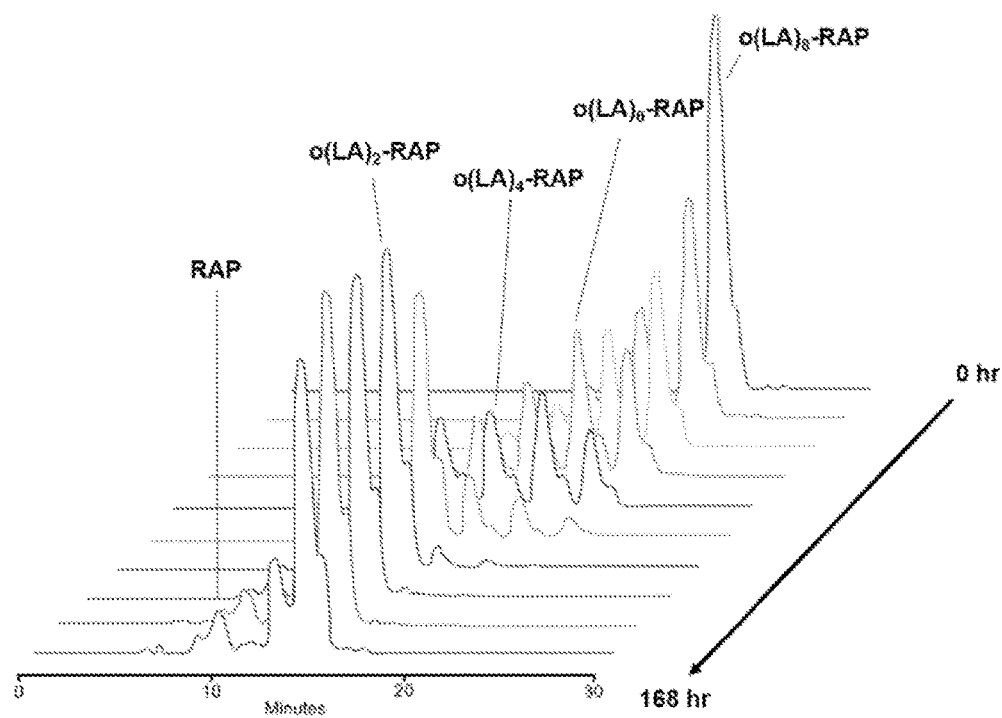
FIGS. 10A and 10B show reverse-phase HPLC chromatograms of o(LA)$_8$-RAP conjugate (10A) and o(LA)$_8$-SEL conjugate (10B) (0.5 mg/mL) and their backbiting conversion products after incubation in 1:1 CH$_3$CN/10 mM PBS at 37° C., pH 7.4 at predetermined time intervals over 168 hours.
Figure 10B:
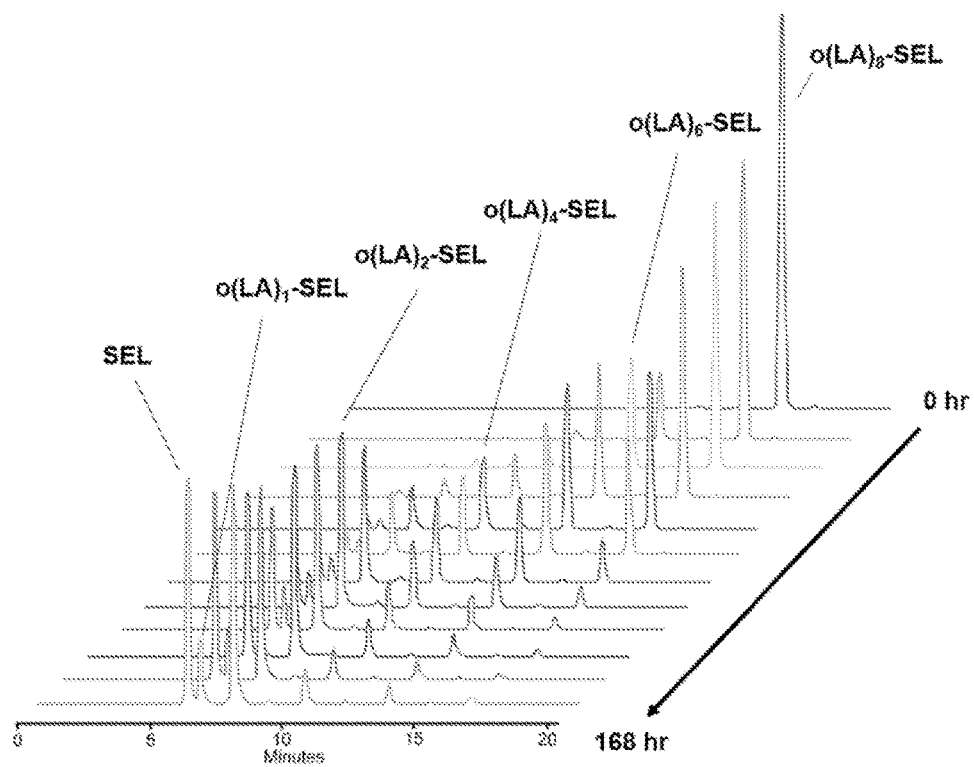
Figure 11A:
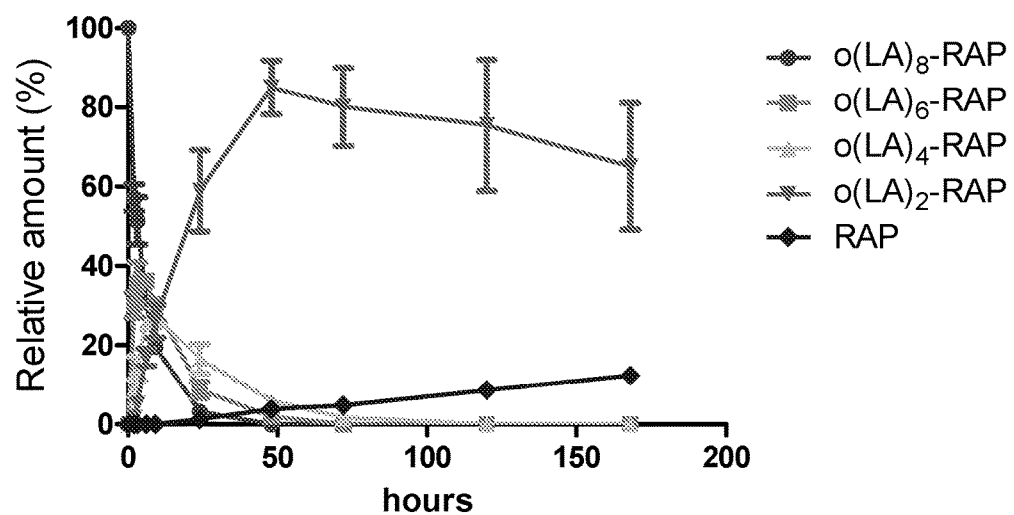
FIGS. 11A and 11B show respectively, a graph showing the time course of the conversion of o(LA)$_8$-RAP conjugate into o(LA)$_6$-RAP, o(LA)$_4$-RAP, o(LA)$_2$-RAP and RAP (mean±SD, n=3) (11A) and a graph showing the time course of the conversion of o(LA)$_8$-SEL conjugate into o(LA)$_6$-SEL, o(LA)$_4$-SEL, o(LA)$_2$-SEL and SEL (mean±SD, n=3) (11B).
Figure 11B:
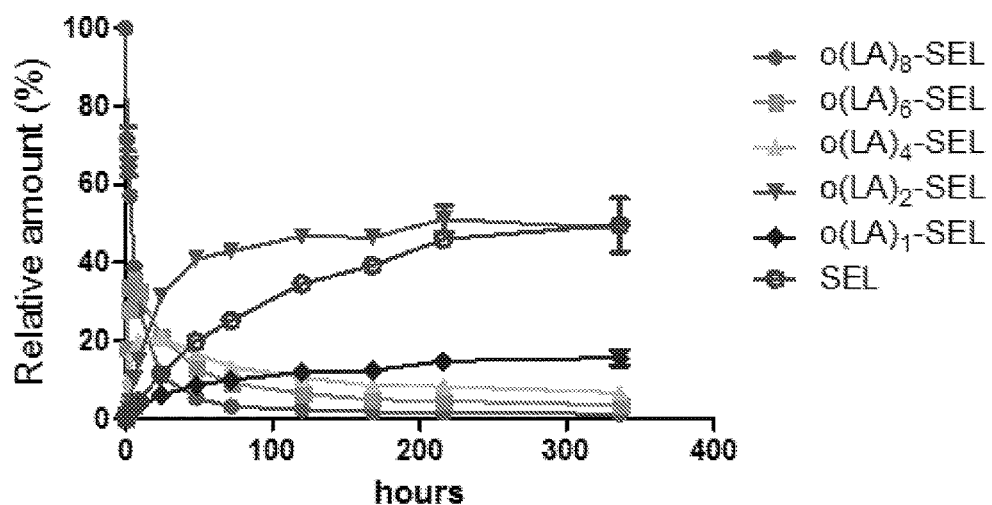

In a 1:1 mixture of acetonitrile and PBS buffer (pH 7.4, 10 mM), used to gain solubility, o(LA)$_8$-PTX conjugate eluted at ca. 23 minutes, and upon conversion, it produced a series of well-defined peaks with shorter elution times, approaching the elution time of PTX, ca. 12 minutes (FIG. 2A). The major peaks were assigned to even number degradation products of o(LA)$_8$-PTX upon the loss of lactoyllactate upon backbiting: o(LA)$_6$-PTX, o(LA)$_4$-PTX, o(LA)$_2$-PTX and PTX, whereas noticeably smaller peaks corresponded to odd number degradation products from random hydrolysis. The relative area (%) of o(LA)$_8$-PTX conjugate, even number degradation products and o(LA)$_1$-PTX were plotted versus time (FIG. 5A). The $t_{1/2}$ for the conversion of o(LA)$_8$-PTX conjugate was ca. 7.3 hours, producing o(LA)$_2$-PTX as the major species and to a lesser extent o(LA)$_1$-PTX and PTX over 300 hours. Similarly, o(LA)$_{16}$-PTX conjugate generated a backbiting degradation profile based on reverse-phase HPLC analysis (FIGS. 2B, 5B): $t_{1/2}$=7.4 hours and even number degradation products, mostly o(LA)$_2$-PTX. On the other hand, conversion of o(LA)$_8$-PTX or o(LA)$_{16}$-PTX conjugates in PEG-b-PLA micelles slowed considerably: $t_{1/2}$=157 and 315 hours, respectively (FIGS. 7A and 7B), consistent with hindered backbiting reaction in a nonpolar environment (PLA core). Conversion of o(LA)$_8$-PTX or o(LA)$_{16}$-PTX conjugates in an aqueous solution appears to proceed rapidly by a backbiting reaction, but slowly in PEG-b-PLA micelles in water. Thus, PEG-b-PLA micelles can stably carry o(LA)$_8$-PTX or o(LA)$_{16}$-PTX conjugate, and upon release, o(LA)$_8$-PTX or o(LA)$_{16}$-PTX conjugate undergoes rapid backbiting, primarily generating o(LA)$_2$-PTX and to a lesser extent o(LA)$_1$-PTX and PTX. Similarly, FIGS. 10A and 11A, provide the conversion of o(LA)$_8$-RAP, and FIGS. 10B and 11B provide the conversion of o(LA)$_8$-SEL.

In Vitro and In Vivo Anticancer Activity of o(LA)$_8$-PTX, o(LA)$_{16}$-PTX, o(LA)$_8$-RAP, and o(LA)$_8$-SEL Conjugates.

Figure 6:
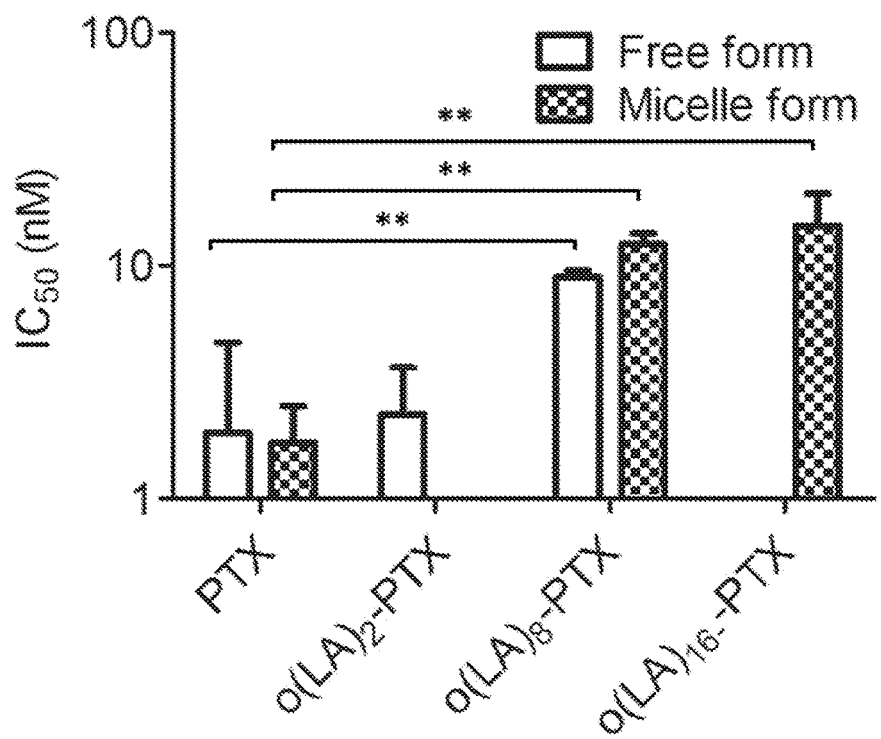
FIG. 6 shows in vitro cytotoxicity of PTX, o(LA)$_2$-PTX, o(LA)$_8$-PTX, and o(LA)$_{16}$-PTX conjugate against human A549 non-small lung cancer cells. Columns: Mean of quadruplicate determinations; bars, SD; **. p<0.01 for o(LA)$_8$-PTX compared to PTX for free and micelle forms.
Figure 12A:
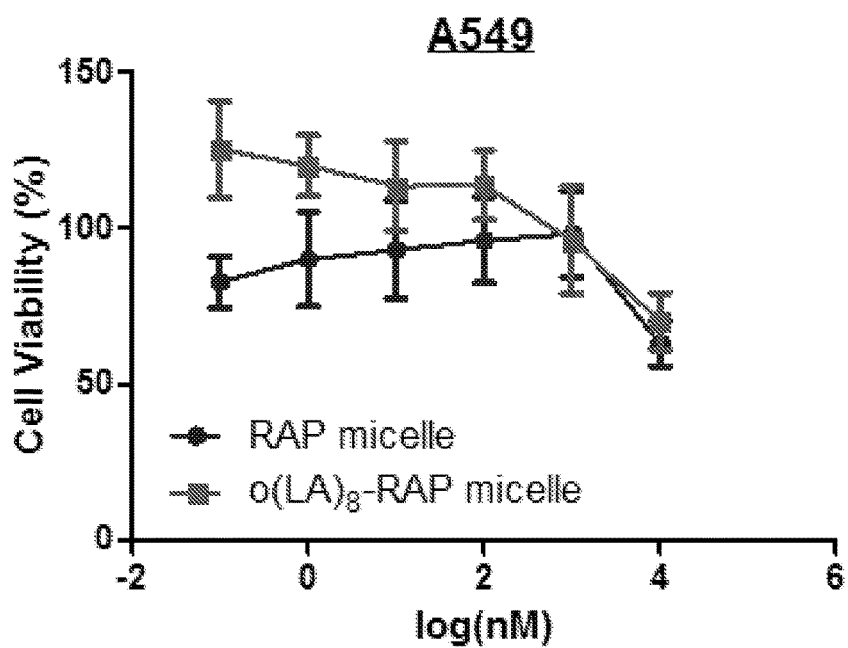
FIG. 12A shows in vitro cytotoxicity of RAP micelles and o(LA)$_8$-RAP conjugate micelles (12A) against human A549 non-small lung cancer cells.
Figure 12B:
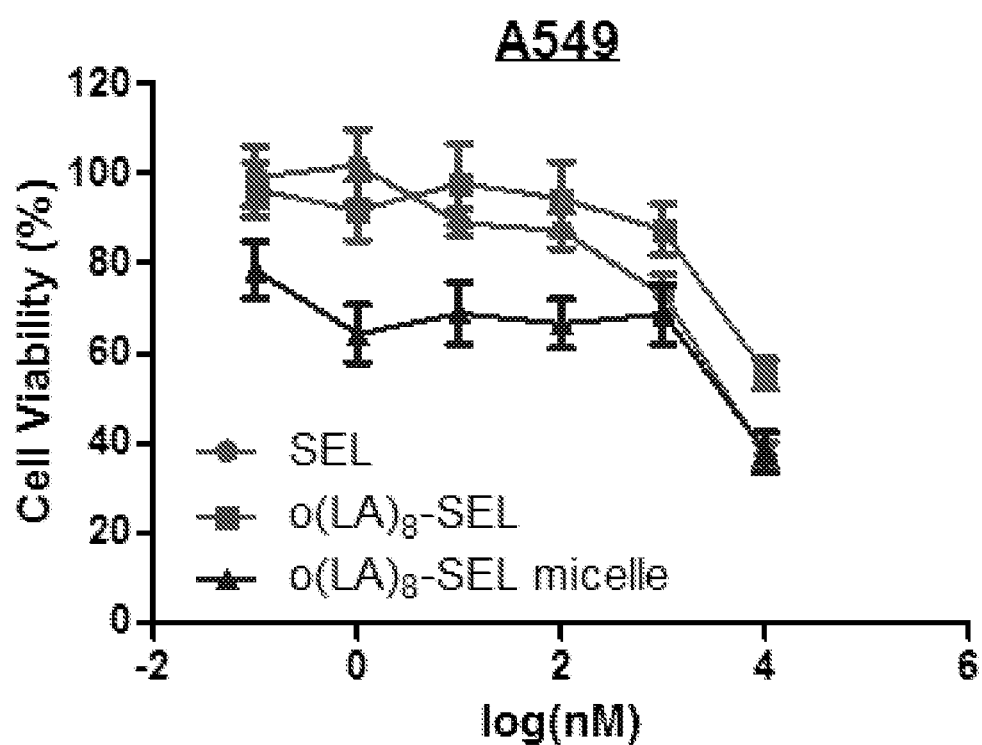
FIG. 12B shows in vitro cytotoxicity of SEL, o(LA)$_8$-SEL conjugate, and o(LA)$_8$-RAP conjugate micelles (12B) against human A549 non-small lung cancer cells.

PTX is a potent anticancer agent as a microtubule stabilizer, and it plays a central role in the treatment of non-small cell lung cancer. Accordingly, PTX had a low IC$_{50}$ value of 2.0 nM for the human A549 non-small cancer cell line (FIG. 6). The IC$_{50}$ value of o(LA)$_8$-PTX in the free form has a slighter higher value of 8.9 nM, reflecting the time needed for conversion. The IC$_{50}$ values of o(LA)$_8$-PTX and o(LA)$_{16}$-PTX as micelles were about 7-fold higher, ca. 15 nM, reflecting the time needed for release from PEG-b-PLA micelles (over 72 hours). Notably, o(LA)$_2$-PTX, the major species generated from backbiting, was equipotent with PTX in vitro. Thus, 2 lactic acid units at the 7-OH position of paclitaxel does not interfere with microtubule stabilization, defining o(LA)$_2$-PTX, o(LA)$_1$-PTX and PTX as bioactive species. By contrast, 2'-OH ester conjugates require full conversion back to PTX for cytotoxicity. In summary, backbiting of o(LA)$_8$-PTX conjugate generates cytotoxic species, primarily o(LA)$_2$-PTX, without a reliance on converting esterases, enabling a novel prodrug strategy for PEG-b-PLA micelles. Similarly, FIGS. 12A and 12B, provide the cytotoxicity of RAP micelle, o(LA)$_8$-RAP micelle, SEL, o(LA)$_8$-SEL, and o(LA)$_8$-SEL micelle compositions.

Figure 8A:
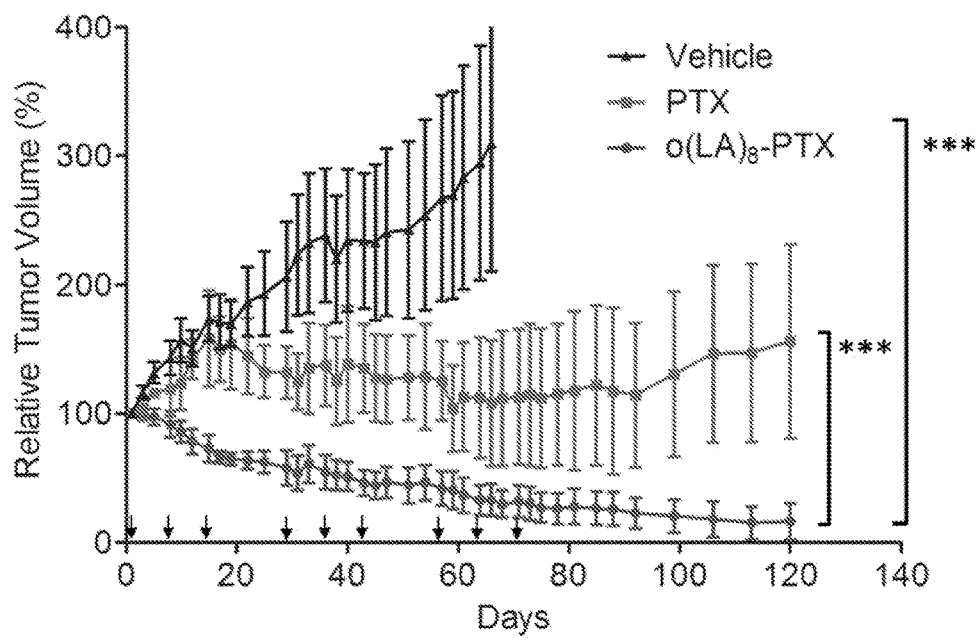
FIG. 8A shows in vivo antitumor efficacy PTX or o(LA)$_8$-PTX conjugate (20 mg/kg) as PEG-b-PLA micelles (9% loading) in an A549 xenograft tumor model. Mice received 3 weekly injections followed by one week off for 3 cycles (mean±SEM, n=3-4). Bars, SEM; *, p<0.001.
Figure 8B:
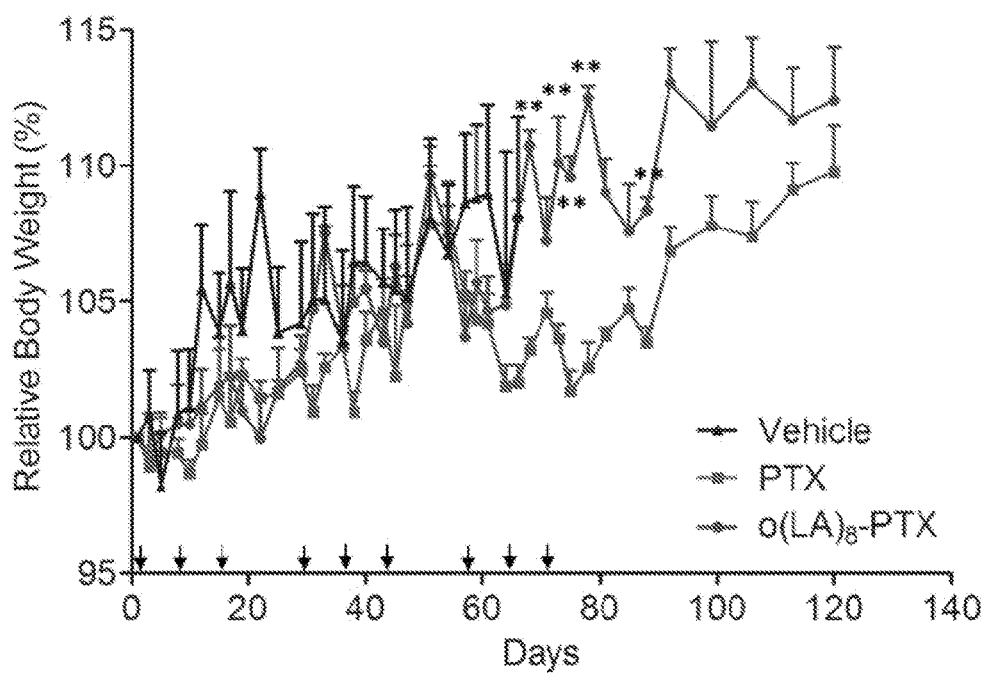
FIG. 8B shows relative body weight of mice treated with PTX or o(LA)$_8$-PTX conjugate (20 mg/kg) as PEG-b-PLA micelles (9% loading). Bars: SEM; , p<0.01.

The in vivo anticancer efficacy of PEG-b-PLA micelles containing PTX or o(LA)$_8$-PTX prodrug was evaluated in an A549 xenograft model after weekly tail vein injection at a dose of 20 mg/kg (FIG. 8). A weekly IV injection schedule for PTX or o(LA)$_8$-PTX conjugate was evaluated because of its clinical relevance (3 weekly injections and one week off×3 cycles). With PEG-b-PLA micelles containing PTX at 20 mg/kg, growth of A549 tumors paralleled the tumor growth of the vehicle control for about 2 weeks, followed by tumor growth inhibition during treatment over 71 days and delayed tumor growth. By contrast, PEG-b-PLA micelles containing o(LA)$_8$-PTX conjugate at 20 mg/kg decreased tumor volumes during weekly treatment over 71 days without relapse up to 120 days (FIG. 8). Surprisingly, o(LA)$_8$-PTX conjugate was also less toxic than PTX in terms of body weight change (FIG. 8).

PTX ester prodrugs are often water soluble and less toxic but less active as anticancer agents. However, the present conjugates with PEG-b-PLA micelles are unique anticancer compositions in terms of backbiting conversion, physical stability, lower toxicity and higher antitumor efficacy in an A549 xenograft model. Given slower in vitro release of the present conjugates versus PTX, these conjugates are expected to reduce the distribution of PTX into non-target tissue, increase tumor exposure (through the EPR effect) and undergo intratumoral conversion by backbiting. The small size of PEG-b-PLA micelles containing the present conjugates (e.g., ca. 30 nm for o(LA)$_8$-PTX) is favorable for the EPR effect, and the low $C_{max}$ of PTX brought about the conjugates favor low host toxicity, especially in comparison to PEG-b-PLA micelles containing PTX (see Cabral, H., et al., *Nat. Nanotechnol.*, 6, 815-823 (2011)).

In vitro anticancer activity of PTX, SEL, and RAP alone and in combination. Table 3 shows the IC$_{50}$ value of PTX, RAP, and SEL in combination is lower than the drugs alone indicating that the 3-drug combination appears to achieve synergy in vitro.

TABLE 3

IC$_{50}$ values and combination index analysis of PTX, SEL, and RAP as alone, 2-drug combination, and 3-drug combination for A549 NSCLC cell line.

| Drug combination | IC$_{50}$ (nM) | CI at F$_a$25 | CI at F$_a$50 | CI at F$_a$75 | CI at F$_a$90 | Molar ratio |
|---|---|---|---|---|---|---|
| PTX | 7.4 ± 1.2 | — | — | — | — | |
| SEL | 1729 ± 1.6 | — | — | — | — | |
| RAP | 320.6 ± 2.3 | — | — | — | — | |
| PTX:SEL | 26.08 ± 1.3 | 0.5 ± 0.1 | 0.5 ± 0.2 | 0.5 ± 0.1 | 0.5 ± 0.2 | 2:3 |
| PTX:RAP | 4.4 ± 1.3 | 0.6 ± 0.3 | 0.6 ± 0.2 | 0.7 ± 0.2 | 0.6 ± 0.4 | 2:1 |
| SEL:RAP | 256.9 ± 1.2 | 0.6 ± 0.1 | 0.6 ± 0.1 | 0.7 ± 0.2 | 0.6 ± 0.2 | 3:1 |
| PTX:SEL:RAP | 27.81 ± 1.1 | 0.3 ± 0.2 | 0.3 ± 0.1 | 0.3 ± 0.1 | 0.4 ± 0.1 | 2:3:1 |

EQUIVALENTS

While certain embodiments have been illustrated and described, a person with ordinary skill in the art, after reading the foregoing specification, can effect changes, substitutions of equivalents and other types of alterations to the conjugates and micelles of the present technology or derivatives, prodrugs, or pharmaceutical compositions thereof as set forth herein. Each aspect and embodiment described above can also have included or incorporated therewith such variations or aspects as disclosed in regard to any or all of the other aspects and embodiments.

The present technology is also not to be limited in terms of the particular aspects described herein, which are intended as single illustrations of individual aspects of the present technology. Many modifications and variations of this present technology can be made without departing from its spirit and scope, as will be apparent to those skilled in the art. Functionally equivalent methods within the scope of the present technology, in addition to those enumerated herein, will be apparent to those skilled in the art from the foregoing descriptions. Such modifications and variations are intended to fall within the scope of the appended claims. It is to be understood that this present technology is not limited to particular methods, reagents, compounds, compositions, labeled compounds or biological systems, which can, of course, vary. It is also to be understood that the terminology used herein is for the purpose of describing particular aspects only, and is not intended to be limiting. Thus, it is intended that the specification be considered as exemplary only with the breadth, scope and spirit of the present technology indicated only by the appended claims, definitions therein and any equivalents thereof.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

In addition, where features or aspects of the disclosure are described in terms of Markush groups, those skilled in the art will recognize that the disclosure is also thereby described in terms of any individual member or subgroup of members of the Markush group. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member.

All publications, patent applications, issued patents, and other documents (for example, journals, articles and/or textbooks) referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

Other embodiments are set forth in the following claims, along with the full scope of equivalents to which such claims are entitled.

What is claimed is:

1. An oligolactic acid conjugate selected from the group consisting of a 7-oligolactic acid conjugate of paclitaxel or a paclitaxel derivative, a 40-oligolactic acid conjugate of rapamycin or a rapamycin derivative, and a 2'-oligolactic acid conjugate of selumetinib or a selumetinib derivative; wherein:
   the oligolactic acid comprises 2 to 24 lactic acid subunits;
   the 7-oligolactic acid is attached through an ester linkage to the oxygen of the 7-hydroxyl of the paclitaxel or paclitaxel derivative;
   the 40-oligolactic acid is attached through an ester linkage to the oxygen of the 40-hydroxyl of the rapamycin or rapamycin derivative; and
   the 2'-oligolactic acid is attached through an ester linkage to the oxygen of the 2'-hydroxyl of the selumetinib or selumetinib derivative.

2. The oligolactic acid conjugate of claim 1 wherein the oligolactic acid comprises 4 to 20 lactic acid subunits.

3. The oligolactic acid conjugate of claim 1 wherein the oligolactic acid comprises 6 to 18 lactic acid subunits.

4. The oligolactic acid conjugate of claim 1 comprising paclitaxel or docetaxel.

5. The oligolactic acid conjugate of claim 1 comprising rapamycin or everolimus.

6. The oligolactic acid conjugate of claim 1 comprising selumetinib, binimetinib, or GDC-0623.

7. A composition comprising water and a micelle comprising a polylactic acid-containing polymer and one or more of the 7-oligolactic acid conjugate, the 40-oligolactic acid conjugate, or the 2'-oligolactic acid conjugate of claim 1.

8. The composition of claim 7 wherein the loading of the 7-oligolactic acid conjugate is from about 5 wt % to about 60 wt %, the loading of the 40-oligolactic acid conjugate is from about 5 wt % to about 50 wt %, and/or the loading of the 2'-oligolactic acid conjugate is from about 2 wt % to about 30 wt %, with respect to the mass of the micelles.

9. The composition of claim 7 wherein the concentration of the 7-oligolactic acid conjugate is from about 0.6 mg/mL to about 40 mg/mL, the concentration of the 40-oligolactic acid conjugate is from about 1 mg/mL to about 20 mg/mL, and/or the concentration of the 2'-oligolactic acid conjugate is from about 0.5 mg/mL to about 15 mg/mL, with respect to the volume of the water in the composition.

10. The composition of claim 7 wherein the composition comprises the 7-oligolactic acid conjugate, the 40-oligolactic acid conjugate, and the 2'-oligolactic acid conjugate.

11. The composition of claim 7 wherein the composition comprises less than about 2 wt % of ethanol, dimethyl sulfoxide, castor oil, and castor oil derivatives based on the weight of the composition.

12. The composition of claim 7 wherein the micelle comprises poly(ethylene glycol)-block-polylactic acid (PEG-b-PLA).

13. The composition of claim 12 wherein the molecular weight of the poly(ethylene glycol) block of PEG-b-PLA is about 1,000 to about 35,000 g/mol and the molecular weight of the poly(lactic acid) block of PEG-b-PLA is about 1,000 to about 15,000 g/mol.

14. The composition of claim 12 wherein the molecular weight of the poly(ethylene glycol) block is about 1,500 to about 14,000 g/mol, the molecular weight of the poly(lactic acid) block is about 1,500 to about 7,000 g/mol.

15. A composition comprising water and a micelle comprising PEG-b-PLA and the oligolactic acid conjugate of claim 1;
   wherein:
      the loading of the 7-oligolactic acid conjugate in the micelle is from about 1 wt % to about 60 wt %; the loading of the 40-oligolactic acid conjugate is from about 1 wt % to about 50 wt %; the loading of the 2'-oligolactic acid conjugate is from about 1 wt % to about 30 wt %, or a combination of two or more thereof, with respect to the mass of the micelles; and
      the molecular weight of the poly(ethylene glycol) block of the PEG-b-PLA is about 1,500 to about 14,000 g/mol, and the molecular weight of the poly(lactic acid) block of the PEG-b-PLA is about 1,500 to about 7,000 g/mol.

16. The composition of claim 15, wherein the composition comprises the 7-oligolactic acid conjugate, the 40-oligolactic acid conjugate, and the 2'-oligolactic acid conjugate.

17. A method of making the oligolactic acid conjugate of claim 1, comprising
   contacting paclitaxel or the paclitaxel derivative having a free 7-hydroxyl group with a coupling agent and a mono-O-silylated oligolactic acid having 2 to 24 lactic acid subunits to form the 7-oligolactic acid conjugate;
   contacting rapamycin or the rapamycin derivative having a free 40-hydroxyl group with a coupling agent and a mono-O-silylated oligolactic acid having 2 to 24 lactic acid subunits to form the 40-oligolactic acid conjugate;
   contacting selumetinib or the selumetinib derivative having a free 2'-hydroxyl group with a coupling agent and a mono-O-silylated oligolactic acid having 2 to 24 lactic acid subunits to form the 2'-oligolactic acid conjugate; or
   a combination of two or more thereof.

18. A method of making the composition of claim 7 comprising:
   combining water with a mixture of a polylactic acid-containing polymer and one or more of the 7-oligolactic acid conjugate, the 40-oligolactic acid conjugate, and the 2'-oligolactic acid conjugate, such that micelles incorporating one or more of the 7-oligolactic acid conjugate, the 40-oligolactic acid conjugate, and the 2'-oligolactic acid conjugate form.

19. The method of claim 18 wherein the polylactic acid-containing polymer is PEG-b-PLA.

20. A method of inhibiting or killing cancer cells sensitive to paclitaxel or a paclitaxel derivative, rapamycin or a rapamycin derivative, and/or selumetinib or a selumetinib derivative comprising contacting the cells with an effective inhibitory or lethal amount of the composition of claim 7.

21. The method of claim 20 wherein the contacting is in vitro.

22. A method of treatment comprising administering to a mammal suffering from a cancer sensitive to paclitaxel or a paclitaxel derivative, rapamycin or a rapamycin derivative, and/or selumetinib or a selumetinib derivative an effective amount of the composition of claim 7.

23. The method of claim 22 wherein the cancer is selected from brain tumors, breast cancer, colon cancer, head and neck cancer, lung cancer, lymphoma, melanoma, neuroblastoma, ovarian cancer, pancreatic cancer, prostate cancer, angiosarcoma, or leukemia.

24. The method of claim 23 wherein the cancer is breast cancer or lung cancer.

25. The method of claim 22 wherein the composition is administered by injection.

* * * * *